United States Patent
Cohen et al.

(12)

(10) Patent No.: US 6,358,736 B1
(45) Date of Patent: Mar. 19, 2002

(54) METHOD FOR INCREASING THE ANTIGEN PRESENTING ABILITY OF LEUKEMIA CELLS

(75) Inventors: Peter A. Cohen, Bethesda, MD (US); Brian J. Czerniecki, Haddenfield, NJ (US); Gary K. Koski; David E. Weng, both of Bethesda, MD (US); Charles Carter, Gaithersberg, MD (US); John O. Ojeifo, Washington, DC (US); Gretchen N. Schwartz, Wheaton, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/401,060

(22) Filed: Sep. 22, 1999

Related U.S. Application Data

(60) Division of application No. 08/885,617, filed on Jun. 30, 1997, now Pat. No. 6,010,905, which is a continuation-in-part of application No. 08/379,227, filed on Jan. 27, 1995, now Pat. No. 5,643,786.

(51) Int. Cl.$^7$ .............................................. C12N 5/08
(52) U.S. Cl. .................... 435/326; 435/7.24; 435/372; 435/383
(58) Field of Search ................. 435/372, 7.24, 435/326, 383

(56) References Cited

U.S. PATENT DOCUMENTS

| | | | |
|---|---|---|---|
| 4,672,044 A | 6/1987 | Schieber | 436/501 |
| 5,643,786 A | 7/1997 | Cohen et al. | 435/325 |

FOREIGN PATENT DOCUMENTS

| | | |
|---|---|---|
| EP | 0563485 A1 | 3/1992 |
| WO | WO 91/13632 | 9/1991 |
| WO | WO 94/02156 | 2/1994 |
| WO | WO 96/23060 | 8/1996 |
| WO | WO 98/06823 | 2/1998 |

OTHER PUBLICATIONS

Glover et al., Journal of Biological Chemistry 270(25): 15359–15367 (1995).*

Fewtrell et al., Biochim. Biophys. Acta 644(2): 363–368 (1981).*

Bernhard, H. et al., "Generation of Immunostimulatory Dendtritic Cells from Human CD34+ Hematopoietic Progenitor Cells of the Bone Marrow and Peripheral Blood", *Cancer Research* 55:1099–1104, 1995.

Chengzheng, L. et al., Chinese Medical Sciences Journal, vol. 6(1), pp. 18–23, Mar. 1991.

Caux, C. et al., "Activation of Human Dendritic Cells through CD40 Cross–linking", *J. Exp. Med.* 180:1263–1272, 1994.

Caux, C. et al., "CD34+ Hematopoietic Progenitors from Human Cord Blood Differentiate Along Two Independent Dendritic Cell Pathways in Response to GM–CSF+ TNFα", *J. Med. Exp.* 184:695–706, 1996.

Cohen PA, et al. Use of interleukin–7, interleukin–2, and interferon–gamma to propagate CD+ T cells in culture with maintained antigen specificity. *J. Immunother.* 14:242–252, 1993.

De Boer, M. et al., Metabolic Comparison Between Basophils and other Leukocytes Human Blood, *The Journal of Immunology.*, 136:3447–3454, 1986.

Esa AH, et al. Immunological heterogeneity of human monocyte subsets prepared by counterflow centrifugation elutriation. *Immunology*, 59:95–99, 1986.

Flores–Romo, L. et al., "CD40 Ligation on Human Cord Blood CD34+ Hematopoetic Progenitors Induces Their Proliferation and Differentiation into Functional Dendtritic Cells", *J. Exp. Med.* 185:341–349, 1997.

Freudenthal PS, et al. The distinct surface of human blood dendritic cells, as observed after an improved isolation method. *Proc. Natl Acad. Sci.* 87:7698–7702, Oct. 1990.

Gieseler, R.K. et al., European Journal of Cell Biology, vol. 54(1), pp. 171–181, 1991.

Hsu, F.J. et al., Vaccination of patients with B–cell lymphoma using autologous antigen–pulsed dendritic cells, *National Medicine*, 2:52–58, 1996.

Klaus, G. et al., "Properties of mouse CD40. Ligation of CD40 activates B cells via a Ca$^{++}$–dependent, FK506–sensitive pathway", *Eur. J. Immunol.* 24:3229–3232, 1994.

Kabel, P. J. et al, Immunobiol., vol. 179(4/5), pp. 395–411, Oct. 1989.

Knight, S..et al., Non–adherent, low–density cells from human peripheral blood contain dendritic cells and monocytes, both with veiled morphology, *Immunology*, 57:595–603, 1986.

Liu, C. et al. Phobol Myristate Acetate and Calcium Ionophore A23187 Modulate the . . . Mouse Dendritic Cells, *Chin Med Sci J.*, 6:18–23, 1991.

Liu, C., et al. , *Biol Abstr* 93(11):AB–686.

(List continued on next page.)

Primary Examiner—Jean C. Witz
(74) Attorney, Agent, or Firm—Knobbe, Martens, Olson & Bear, LLP

(57) ABSTRACT

The present invention relates to methods of increasing the antigen presenting ability of leukemia cells by contacting them with an agent which increases the intracellular calcium level. Methods of treating leukemia are also disclosed.

31 Claims, 15 Drawing Sheets

OTHER PUBLICATIONS

Mehta–damani A. et al., Generation of antigen–specific CD8+ CTLs from naive presursors. *J. Immunol.* 153:996–1003, 1994.

Nijman, H.W. et al., Antigen Capture and Major Histocompatibility Class II Compartments of Freshly Isolated and Cultured Human Blood Dendritic Cells, *J. Exp. Med.* 182:163–174, 1995.

Nishioka, Y. et al., "The Role of CD40–CD40 Logand Interaction in Human T Cell—B Cell Collaboration", *J. Immunol.* 153:1027–1036, 1994.

Ossevoort, M.A. et al., Dendritic Cells in Fundamental and Clinical Immunology, Edited by Kamperdijk et al., Plenum Press, New York, N.Y., pp. 185–189, Jul., 1993.

Ossevoort, et al., A rapid isolation procedure for dendritic cells from mouse spleen by centrifufal elutriation. *J. Immunol. Methods* 155:101–111, 1992.

Peters, J. H. et al., "Dendritic cells: from ontogenetic orphans to myelomonocytic descendants", *Immunol. Today* 17:273–278, 1996.

Peters, J. H. et al., "Pathobiology." vol. 59, 1991, pp. 122–126.

Pickl, W.F. et al., "Molecular and Functional Characteristics of Dendritic Cells Generated from Highly Purified CD14+ Peripheral Blood Monocytes", *J. Immunol.* 157:3850–3859, 1996.

Rober, R.A. et al., Experimental Cell Research, vol. 190(2), pp. 185–194, Oct. 1990.

Romani, N.. et al., Proliferating dendritic cell progenitors in human blood. *J. Exp. Med.* 180:83–93, Jul., 1994.

Seino, K. et al., "CD86 (B70/B7–2) on endothelial cells co–stimulates allogeneic $CD4^+$ T cells" *Int. Immunol.* 7:1331–1337, 1995.

Spear, G.T. et al., "Oxidative Burst Capability of Human Monocyte Subsets Defined by High and Low HLA–DR Expression," *Immunological Investigations*, vol. 18(8), pp. 993–1005, 1989.

Szaboles, P. et al., "Dendritic Cells and Macrophages Can Mature Independently From a Human Bone Marrow—Derived, Post—Colony–Forming Unit Intermediate", *Blood* 87:4520–4530, 1996.

Thomas, R. et al., "Isolation and Characterization of Human Blood Peripheral Blood Dendritic Cells", *J. Immunol.* 150:821–834, 1993.

Thomas, R. et al., "Human Peripheral Blood Dendritic Cells Subsets" *J. Immunol.* 153:4016–4028, 1994.

Thomas, R. et al., Comparative accessory cell function of human peripheral blood dendritic cells and monocytes. *J. Immunol.* 151:6840–6852, No. 12, Dec. 1993.

Zhou, L. et al., "$CD14^+$ blood monocytes can differentiate into functionally mature $CD83^+$ dendritic cells", *Proc. Natl. Acad. Sci. U.S.A.* 93:2588–2592, 1996.

Klein, J.B., et al., The J. of Immunology, vol. 144(11), pp. 4305–4311.

Nusslein, H.G., et al., Eur. J. Immunol., vol. 26(4), pp. 846–850.

Tyers, M., et al., FEBS Lett., vol. 206(1), pp. 99–105, (abstract only at this time).

Yonish–Rouach, E., et al., Cell. Immunol., vol. 134(2), pp. 402–413, (abstract only at this time).

Weber, C., et al., Eur. J. of Immunol., vol. 23(4), pp. 852–859 (abstract only at this time).

Sigma BioSciences 1996 Cell Culture Catalogue and Price List, pp. 56–65.

Ina, Y., et al., The J. of Immunol., vol. 139(5), pp. 1711–1717.

Gerli, R., et al., The J. of Immunol., vol. 142(8), pp. 2583–2589.

Cai, J.P., et al., Cell. Immunol., vol. 167(2), pp. 269–275.

International Search Report for PCT/US 98/13542, mailing date Mar. 17, 1999.

Dialog Information Service, File 154, Medline, Dialog Accession No. 06943165, Medline Accession No. 91235804, Gieseler RK et al: "Dendritic Accessory Cells Derived from Rat Bone Marrow Precursors Under Chemically Defined Conditions in Vitro Belong to the Myeloid Lineage", Eur J. Cell BNIO. (Germany) 54(1): 171–181 (Feb. 1991).

Dialog Information Service, File 35, Dissertation Abstracts Online, Dialog Accession No. 01501749, Shen, Hong Ming: "The Effects of Cocaine on Mouse Macrophage Biology (Calcium)", 57(04–B) of Dissertation Abstracts International, p. 2467 (1996).

Dialog Information Service, File 154, Medline, Dialog Accession No. 06925784, Medline Accession No. 91347480, Liu, C., et al.: "The Enhancing Effect of Calcium Ionophore A23187 on the Accessory Function of Mouse Dendritic Cells", (China) 13(3), (1991).

Celluzzi, C.M., et al., J. Exp. Med., "Peptide–pulsed Dendritic Cells Induce Antigen–specific, CTL–mediated Protective Tumor Immunity", vol. 183, pp. 283–287, Jan. 1996.

Donnadieu, E., et al., Current Biology, "Antigen Recognition by Helper T Cells Elicits a Sequence of Distinct Changes ot their Shape and Intracellular Calcium", vol. 4, No. 7, pp. 584–595, 1994.

Engleman, Edgar G., Cytotechnology, "Dendritic Cells: Potential Role in Cancer Therapy", vol. 25, pp. 1–8, 1997.

Flamand, V., et al., Eur. J. Immunol., "Murine Dendritic Cells Pulsed in Vitro with Tumor Antigen Induce Tumor Resistance in Vivo", vol. 24, pp. 605–610, 1994.

Hsu, F., et al., Nature Medicine, "Vaccination of Patients with B–cell Lymphoma using Autologous Antigen–Pulsed Dendritic Cells", vol. 2, No. 1, pp. 52–58, Jan. 1996.

Liu, C., et al., Dialog File 154, Database Medline, US National Library of Medicine, "The Enhancing Effect of Calcium Ionophore A23187 on the Accessory Function of Mouse Dendritic Cells" Accession No. 06925784.

Liu, Si–Qiong J., et al., Biophysical Journal, "T–Cell Stimulation through the T–Cell Receptor/CD3 Complex Regulates CD2 Lateral Mobility by a Calcium/Calmodulin–Dependent Mechanism", vol. 76, pp. 1679–1692, Mar. 1999.

Negulescu, P.A., et al., Immunity, "Polarity of T Cell Shape, Motility, and Sensitivity to Antigen", vol. 4, pp. 421–430, May 1996.

Shen, Hong Ming, Dialog File 35, Database Medline, US National Library of Medicine, "The Effects of Cocaine on Mouse Macrophage Biology (Calcium)", Accession No. 01501749.

\* cited by examiner

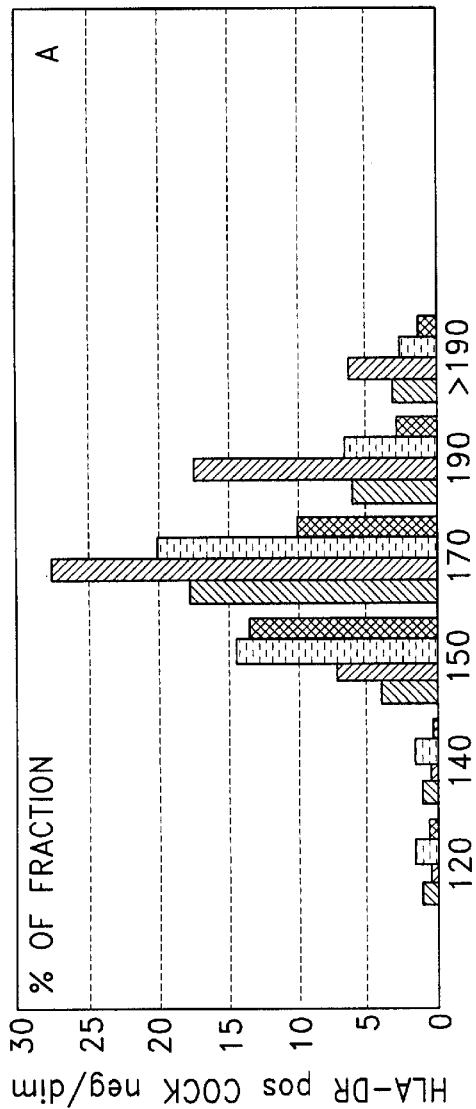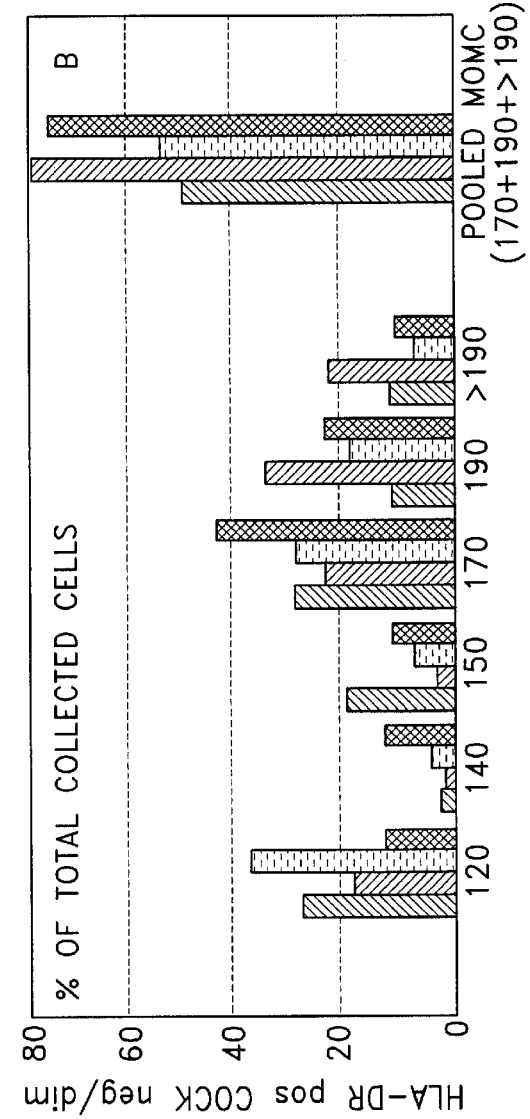
FIG. 1A
FIG. 1B

CD14 POS
UNTREATED

CD14 NEG/DIM
UNTREATED

CD14 POS
A23187 TREATED

CD14 NEG/DIM
A23187 TREATED

CD14 POS
UNTREATED

CD14 NEG/DIM
UNTREATED

CD14 POS
A23187 TREATED

CD14 NEG/DIM
A23187 TREATED

CD14 POS
UNTREATED

CD14 NEG/DIM
UNTREATED

CD14 POS
A23187 TREATED

CD14 NEG/DIM
A23187 TREATED

CD14 POS
UNTREATED

CD14 NEG/DIM
UNTREATED

CD14 POS
A23187 TREATED

CD14 NEG/DIM
A23187 TREATED

CD14 POS
UNTREATED

CD14 NEG/DIM
UNTREATED

CD14 POS
A23187 TREATED

CD14 NEG/DIM
A23187 TREATED

CD14 POS
UNTREATED

CD14 NEG/DIM
UNTREATED

CD14 POS
A23187 TREATED

CD14 NEG/DIM
A23187 TREATED

CD14 POS
UNTREATED

CD14 NEG/DIM
UNTREATED

CD14 POS
A23187 TREATED

CD14 NEG/DIM
A23187 TREATED

METHOD FOR INCREASING THE ANTIGEN PRESENTING ABILITY OF LEUKEMIA CELLS

RELATED APPLICATIONS

This application is a divisional of U.S. patent application Ser. No. 08/885,671, filed Jun. 30, 1997, now U.S. Pat. No. 6,010,905, which is a continuation-in-part of U.S. patent application Ser. No. 08/379,227 filed Jan. 27, 1995, now U.S. Pat. No. 5,643,786, the disclosures of which are incorporated herein by reference in their entireties.

BACKGROUND OF THE INVENTION

Antigen presenting cells (APCs) are naturally occurring cells whose function is to present both "self" and "foreign" proteins (antigens) to the immune system. When antigens are effectively presented by APCs, they can activate T lymphocytes to recognize and fight infections as well as some types of cancer (Shimizu, J. et al. 1991 *J Immunol.* 146:1708–1714; Zou, J. et al. 1992 *Cancer Immunol. Immunother.* 35:1–6; Takahashi, H. et al. 1993 *International Immunology* 5:849–857). Antigen-pulsed APCs have traditionally been prepared in one of two ways: (1) small peptide fragments, known as antigenic peptides, are "pulsed" directly onto the outside of the APCs (Mehta-Damani, A. et al. 1994 *J. Immunol.* 153:996–1003); or (2) APCs are incubated with whole proteins or protein particles which are then ingested by the APCs. These proteins are digested into small peptide fragments by the APC and eventually carried to and presented on the APC surface (Cohen, P A et al. 1994 *Cancer Res.* 54:1055–1058).

After APCs are prepared by one of the above methods, they can be injected back into a patient as a "vaccine," eventually reaching locations such as lymph nodes where they present the desired antigen to T lymphocytes (Inaba, K. et al. 1990 *J. Exp. Med.* 172:631–640 1990 [published erratum appears in *J. Exp. Med.* 1990 172(4):1275]). In another treatment, T lymphocytes are removed from a patient and stimulated to grow in culture by contact with the APCs (Cohen, P A et al. 1993 *J. Immunother.* 14:242–252). This latter approach can be used to propagate large numbers of "antigen specific" T lymphocytes which can be given to the patient as "adoptive immunotherapy."

An effective APC has several important properties: (1) it retains the peptide antigen on its cell surface long enough to present it to T lymphocytes; (2) it should process (ingest and digest) whole proteins or particles into peptide fragments as described above; (3) it can be activated to express additional "costimulatory" and adhesion molecules on its surface membrane which help T lymphocytes respond appropriately after encountering antigen on the APC surface. Because effective antigen presentation requires a complicated system of cellular signals, researchers have concentrated on collecting human cells whose primary natural function is antigen processing and presentation. While a wide variety of cell types such as monocytes, macrophages, B cells and dendritic cells have a demonstrated ability to present antigen, extensive evidence indicates that the dendritic cell (DC) is nature's most potent antigen-presenting cell. DCs can express all of the necessary costimulatory and presentation molecules with great flexibility. In addition, dendritic cells' only known function is antigen presentation. While other types of APCs are capable of resensitizing T lymphocytes to previously encountered antigens (so-called "recall" antigens), DCs are thought to be most responsible primary for sensitization of T lymphocytes (Croft, M. et al. 1994 *J. Immunol.* 152:2675–2685).

DCs are derived from "myeloid precursor" cells in the bone marrow which also give rise to monocytes and macrophages (Thomas, R. et al. 1994 *J. Immunol.* 153:4016–4028). It is also possible that monocytes themselves serve in vivo as immediate precursors to dendritic cells and macrophages. As support for this theory, researchers have found that monocytes are capable of developing into cells morphologically and immunophenotypically identical to either DCs or macrophages in culture. This finding indicates that lymphocytes which share the same bone marrow precursor are relatively uncommitted to a particular differentiation pathway for at least some portion of their development (Peters, J H et al. 1991 *Pathobiology* 59:122–126; Pickl et al,. *J. Immunol.* 157:3850, 1996; Zhou and Tedder, *Proc. Natl. Acad. Sci. U. S. A.* 93:2588, 1996).

Because DCs are derived from the bone marrow, they must travel through the blood until they reach their destination organs. These target organs include virtually every organ in the body. Due to this essential transit through the blood, the blood itself is the richest available source of DCs in the human body. It has been estimated that 1–3% of all mononuclear blood cells are precommitted DCs (Thomas, R. et al. 1993 *J. Immunol.* 151:6840–6852). The 10–15% of peripheral blood mononuclear cells which are monocytes, and which are typically present in ten fold greater numbers than dendritic cells, may also, at least in part, have the potential to differentiate into DCs (Peters, J H et al. 1991 *Pathobiology* 59:122–126).

A number of strategies have been developed by others to isolate and purify human DCs from peripheral blood. The two fundamental approaches involve (1) isolating bone marrow precursor cells ($CD34^+$) from blood and stimulating them to differentiate into DCs; or (2) collecting the precommitted DCs from peripheral blood. While the first approach is of great theoretic interest, the patient must unadvantageously be treated with cytokines such as GM-CSF to boost the number of circulating $CD34^+$ stem cells in the peripheral blood. Moreover, the procedures necessary to generate large numbers of DCs are costly and lengthy, and the function of DCs obtained in this fashion has not yet been proved adequate for many applications (Romani, N. et al. 1994 *J. Exp. Med.* 180:83–93; Bernhard, H. et al. 1995 *Cancer Res.* 55:1099–1104). In addition, exposing antigen presenting cells, such as dendritic cells, in culture to foreign proteins such as fetal calf serum can cause them to preferentially present these unwanted antigens.

The second approach for isolating DCs is to collect the relatively large numbers of precommitted DCs already circulating in the blood. Previous techniques for preparing mature DCs from human peripheral blood have involved combinations of physical procedures such as metrizamide gradients and adherence/nonadherence steps (Freudenthal, P S et al. 1990 *Proc. Natl. Acad. Sci.* 87:7698–7702); Percoll gradient separations (Mehta-Damani, et al. 1994 *J. Immunol.* 153:996–1003); and fluorescence activated cell sorting techniques (Thomas, R. et al. 1993 *J. Immunol.* 151:6840–6852). All of these methods are uniformly plagued by small final DC yields, quality control problems and/or probable functional alterations of the DCs due to physical trauma and the extended period of time required to complete these procedures.

One technique for separating large numbers of cells from one another is known as countercurrent centrifugal elutriation (CCE). In this technique, cells are subject to simultaneous centrifugation and a washout stream of buffer which is constantly increasing in flow rate. The constantly increasing countercurrent flow of buffer leads to fractional cell separations that are largely based on cell size.

It was demonstrated over ten years ago that when human blood mononuclear cells were separated by countercurrent centrifugal elutriation (CCE) into two basic fractions, then called "lymphocyte fraction" and "monocyte fraction," that the "monocyte" fraction possessed the ability to present a recall antigen, tetanus toxoid, to the "lymphocyte" fraction (Esa, A H et al. 1986 *Immunology* 59:95–99). However, these investigators did not attempt to use elutriation to specifically isolate dendritic cells from the peripheral blood. Additionally, these investigators did not question whether the monocyte fraction could sensitize T lymphocytes to antigens never previously encountered ("primary in vitro sensitization").

In experiments performed between 1992 and 1994, we performed CCE in the "traditional" manner. As was known, CCE separates cells by their size. Cell fractions were taken from the elutriation rotor at specific buffer flow rates, while the rotor spins at a constant rate. During the procedure, the buffer is constantly increasing in flow rate. In these previous experiments, we elutriated cell fractions from the rotor at a constant centrifugal speed of 3000 rpm. The following fractions were isolated in the traditional manner.

- a "140" fraction (traditional lymphocyte fraction) was collected and used as a source of lymphocytes. This fraction was elutriated at a buffer flow rate of 140 cc/min.
- a "150" fraction, known as "intermediate" was discarded as is traditionally customary. This fraction was elutriated at a buffer flow rate of 150 cc/min.
- a "rotor off (R/0)" fraction (traditional "monocyte" fraction) was collected and used as a source of APCs. This fraction was collected by eluting the cells remaining in the initial sample after the rotor has stopped.

Following elutriation, each fraction was either utilized immediately or cryopreserved in 10% DMSO so it could be stored and thawed for use at later times. However, as with prior attempts to isolate dendritic cells from other blood cells, elutriation per se did not result in marked enrichment for dendritic cells. In a typical experiment, we only found a 2–3 fold enrichment of dendritic cells in the traditional rotor off fraction. Therefore, additional isolation techniques would still have been necessary to isolate purified dendritic cells.

Other cell isolation techniques have additionally used fluorescent activator cell sorting (FACS) to subselect DCs from other peripheral blood cells (Thomas, R. et al. 1994 *J. Immunol.* 153:4016–4028; Thomas, R et al. 1993 *J. Immunol.* 151:6840–6852). However, all of these methods have inherent disadvantages. The final yields are relatively small, indicating losses of most of the initial DCs during inefficient and potentially traumatic purification processes.

Further, these methods are extremely time-consuming and prone to quality control problems. During these procedures purified DCs may lose the ability to process antigen effectively after undergoing several days of mechanical purifications and/or FACS manipulations. Mouse studies of dendritic cell isolation have demonstrated that enrichment methods which require several hours rather than days result in a more fully functional DC collection (Girolomoni, G. 1990 *J. Immunol.* 145:2820–2826). In addition, monocytes, themselves a potential precursor of DCs, are lost in the purification process since they are part of the discarded 150 fraction.

Some investigators have shown rapid methods of isolating dendritic cells from mouse spleen cells by centrifugal elutriation followed by FACS analysis (Ossevoort, Mass. et al. 1992 *J. Immunol. Methods* 155(1):101–11). However, such rapid collection techniques have not been used to isolate dendritic cells from peripheral blood. In addition, a large number of the monocytes that co-migrate upon countercurrent centrifugal elutriation are wasted because there is no reliable method of isolating immunologically activated dendritic cells from monocytes. Therefore, a need exists for a method of isolating dendritic cells that results in large yields, but is quick and efficient. Further, a method of converting monocytes to dendritic cells needs to be developed to increase the yield of dendritic cells isolated from the peripheral blood.

SUMMARY OF THE INVENTION

One embodiment of the present invention is a method of increasing the antigen presenting ability of leukemia cells comprising contacting said leukemia cells with an agent which elevates the intracellular calcium concentration to a level sufficient to increase said antigen presenting ability. In one aspect of this embodiment, the agent comprises a calcium ionophore. For example, the calcium ionophore is selected from the group consisting of A23187 and ionomycin. In another aspect of this embodiment, the leukemia cells increase their level of expression of B7.1. In a further aspect of this embodiment, the leukemia cells increase their level of expression of B7.2. In still a further aspect of this embodiment, the leukemia cells increase their level of expression of ICAM-1. In another aspect of this embodiment, the leukemia cells increase their level of expression of CD83. In still another aspect of this embodiment, the leukemia cells increase their level of expression of B7.1, B7.2, and ICAM-1. The leukemia cells may also express B7.1, B7.2, ICAM-1 and CD83. In some aspects of this embodiment, the leukemia cells are myeloid leukemia cells. In other aspects of this embodiment, the leukemia cells are lymphoid leukemia cells. The method may further comprise contacting T cells with leukemia cells which have been treated with said agent.

Another embodiment of the present invention is a method of increasing the antigen presenting ability of leukemia cells comprising obtaining a population of cells from a subject comprising leukemia cells in order to increase the antigen presenting ability of the leukemia cells and contacting the leukemia cells with an agent which elevates the intracellular calcium concentration to a level sufficient to increase the antigen presenting ability of said leukemia cells. In one aspect of this embodiment, the agent comprises a calcium ionophore. In another aspect of this embodiment, the leukemia cells increase their level of expression of B7.1. In a further aspect of this embodiment, the leukemia cells increase their level of expression of B7.2. In another aspect of this embodiment, the leukemia cells increase their level of expression of ICAM-1. In another aspect of this embodiment, the leukemia cells increase their level of expression of CD83. In another aspect of this embodiment, the leukemia cells increase their level of expression of B7.1, B7.2, and ICAM-1. In a further aspect of this embodiment, the agent elevates the intracellular calcium level by blocking the export of calcium out of the cytoplasm. In some aspects of this embodiment, the agent comprises adenovirus. In another aspect of this embodiment, the calcium ionophore is selected from the group consisting of A23187 and ionomycin. In a further aspect of this embodiment, the agent activates the calcineurin pathway. In another aspect of this embodiment, the method further comprises contacting said leukemia cells which have been contacted with said agent with a compound selected from the group consisting of rhGM-CSF and IFN-gamma. In another aspect of this embodiment, the method further comprises contacting said leukemia cells which have been contacted with said agent with a compound selected from the group consisting of glucocorticoids, prostaglandins, and TGF-beta. In another aspect of this embodiment, the method further comprises contacting said leukemia cells which have been contacted with said agent with endotoxin. In still another aspect of this embodiment, the method further comprises the step of contacting T cells with said leukemia cells which have been contacted with said agent. In yet a further aspect of this embodiment, the method further comprises measuring the antigen presenting ability of said leukemia cells which have been contacted with said agent. In some aspects, the method further comprises the step of transferring said leukemia cells which have been contacted with said agent to a subject. In another aspect of this embodiment, the obtaining step comprises obtaining said leukemia cells from said subject. The method may further comprise treating said leukemia cells with an agent which prevents them from replicating.

Another aspect of this embodiment is a method for obtaining leukemia cells having a desired pattern of MHC Class I cell surface markers comprising contacting the leukemia cells with an agent which elevates the intracellular calcium level to a sufficient level to provide said desired level of MHC Class I cell surface markers.

BRIEF DESCRIPTION OF THE DRAWINGS

FIG. 1A shows the percentage of peripheral blood mononuclear cells in individual elutriation fractions which had the phenotype of immature dendritic cells.

FIG. 1B shows the percentage of total leukapheresed cells in each elutriation fraction with the phenotype of immature dendritic cells.

FIGS. 6Y–6AB show the CD83 expression patterns of purified $CD14^{pos}$ cells cultured in medium alone, purified $CD14^{neg/dim}$ cells cultured in medium alone, purified $CD14^{pos}$ cells cultured with 750 ng/ml A23187, and purified $CD14^{neg/dim}$ cells cultured with 750 ng/ml A23187.

DETAILED DESCRIPTION OF THE PREFERRED EMBODIMENT

Figure 2A:
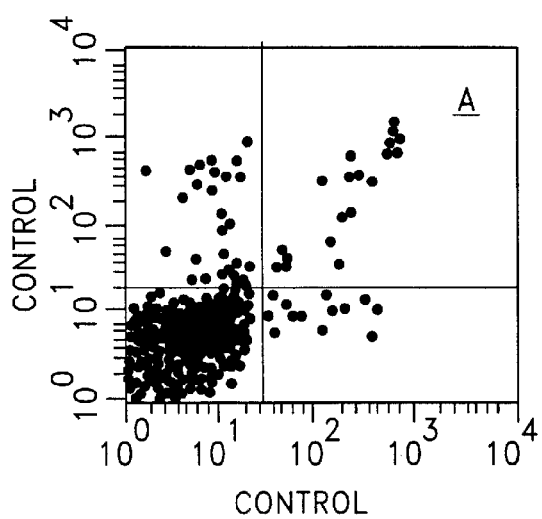
FIG. 2A is a FACS analysis of pooled MOMC stained with mouse IgG subclass matched phycoerythrin (PE) and FITC conjugated control Ab.

The present invention relates to methods of inducing cells to exhibit the phenotype of activated myeloid dendritic cells and methods for preparing the cells which are to be induced to exhibit that phenotype. A variety of cell types may be induced to exhibit the phenotype of activated myeloid dendritic cells, including monocytes, pluripotent bone marrow cells, and cancer cells. Each of these cell types may be induced to rapidly exhibit the phenotype of activated myeloid dendritic cells by contacting the cells with an effective amount of an agent which raises the intracellular calcium concentration to a level sufficient to induce that phenotype.

While both monocytes and immature dendritic cells express the myeloid markers CD13 (Leu M7) and CD33 (Leu M9), they differ with regard to CD14 (Leu M3), an LPS receptor abundantly expressed by monocytes but not (or at a much lower density) by immature dendritic cells. Peters, J. H., R. Gieseler, B. Thiele, and F. Steinbach. 1996. Dendritic cells: from ontogenetic orphans to myelomonocytic descendents. *Immunol. Today* 17:273; Thomas, R., L. S. Davis, and P. E. Lipsky. 1993. Comparative accessory cell function of human peripheral blood dendritic cells and monocytes. *J. Immunol.* 151:6840. Thomas, R., L. S. Davis, and P. E. Lipsky. 1993. Isolation and characterization of human peripheral blood dendritic cells. *J. Immunol.* 150:821; Thomas, R. and P. E. Lipsky. 1994. Human peripheral blood dendritic cell subsets. Isolation and characterization of precursor and mature antigen-presenting cells. *J. Immunol[<m]ed. 153:4016;* Nijman, H. W., M. J. Kleijmeer, M. A. Ossevoort, V. M. Oorschot, M. P. Vierboom, M. van de Keur, P. Kenemans, W. M. Kast, H. J. Geuze, and C. J. Melief. 1995. Antigen capture and major histocompatibility class II compartments of freshly isolated and cultured human blood dendritic cells. *J. Exp. Med.* 182:163. In addition, methods for obtaining the cells which are to be induced to exhibit the phenotype of activated myeloid dendritic cells were developed. One method involves countercurrent centrifugal elutriation. Cells to be induced to express the phenotype of activated myeloid dendritic cells may also be prepared by Ficoll separation followed by monocyte enrichment by plastic adherence. In addition, unfractionated preparations of peripheral blood mononuclear cells may also be induced to express the phenotype of activated dendritic cells. Each of these methods is described below.

I. Preparation of Monocytes by Countercurrent Centrifugal Elutriation

One method for preparing cells to be induced to exhibit the phenotype of activated myeloid dendritic cells involves use of leukapheresis to initially isolate neutrophil-depleted, platelet rich blood cells from a donor. Leukapheresis involves continuously extracorporealizing blood from a donor using laminar flow properties to separate mononuclear (white) cells and platelets from red cells and plasma. The unneeded red cells and plasma are returned to the patient during the leukapheresis procedure. With this technique, the white cells and platelets are selectively removed from many liters of a donor's blood over a several hour period without harming the donor.

During the development of our method, we found that a rinse of EDTA-free, $Ca^{++}/Mg^{++}$ free citrate buffer following leukapheresis dramatically increased the final yield of dendritic cells. We believe that this is due to rinsing away of contaminating proteins, cell fragments and calcium from the leukaphereis procedure. While the use of a citrate buffer is preferred, other cold buffers known in the art could be substituted without departing from the spirit of this feature of the invention.

Following a rinse with a citrate buffer, we perform countercurrent centrifugal elutriation (CCE) on the enriched collection of blood cells from leukapheresis. CCE more specifically isolates monocytes and dendritic cells from other white blood cells. As explained above, countercurrent centrifugal elutriation is a technique whereby the cells are subject to simultaneous centrifugation and a washout stream of buffer which is constantly increasing in flow rate. The constantly increasing countercurrent flow of buffer leads to fractional cell separations that are largely based on cell size. The present invention exploits the selection mechanism of CCE in conjunction with leukapheresis to result in high purity dendritic cell preparations.

During our procedures, it became apparent that the majority of peripheral blood dendritic cells in a sample could be consistently collected without neutrophil contamination in a newly defined "Antigen Presenting Cell Fraction". This fraction consisted of 92–95% monocytes and 5–8% dendritic cells, with the absolute number of dendritic cells being the vast majority of those present in the patient's peripheral blood sample. On a typical pheresis/elutriation collection, this fraction would represent a yield of $1-1.5\times10^8$ partially purified dendritic cells, at least ten fold greater numbers than any other published method (Freudenthal, P. S. et al. 1990 *Proc. Natl. Acad. Sci.* 87:7698–7702; Romani, N. et al. 1994 *J. Exp. Med.* 180:83–93; Thomas, R. et al. 1993 *J. Immunol.* 151:6840–6852; Mehta-Damani, A. et al. 1994 *J. Immunol.* 153:996–1003). While this large dendritic cell subpopulation could then be separated from the monocytes in a number of ways, including a FACS sort, the advisability of such a separation was unclear. Some investigators had reported that monocytes themselves could develop dendritic morphology and function in the presence of certain cell culture media or cytokines, notably IL-4 (Peters, J. H., et al. 1991 *Pathobiology* 59:122–126; Pickl et al,. *J. Immunol.* 157:3850, 1996; Zhou and Tedder, *Proc. Natl. Acad. Sci. U. S. A.* 93:2588, 1996).

Therefore, we decided to formulate an additional method of developing a reliable means to convert the bulk monocyte population to a cellular phenotype indistinguishable from activated dendritic cells. As part of this investigation, we discovered that calcium ionophore could be used to convert isolated monocytes into functional dendritic cells. This converted monocyte population, once added to the isolated dendritic cell population, could provide a typical total dendritic cell yield of $1-1.5\times10^9$ cells, which was 100–1000 fold greater than any other published method. This feature of the invention is discussed in greater detail below.

As described in more detail below, the pattern of surface marker expression characteristic of dendritic cells was characterized a FACS technique that would detect and measure DC subpopulations present in each elutriation fraction from fresh peripheral blood was developed. This involved simultaneously staining the cells with a cocktail of fluorescent antibodies of one color (e.g., fluorescein) to markers that are absent from DCs (e.g. CD3, CD20, CD56 and CD14) and additional antibodies of a different color (e.g. phycoerythrin) that are known to be present on, but not unique to dendritic cells (HLA-DR, B7.2, CD13/33, etc.) This negative cocktail plus positive marker approach enabled demonstration of a unique subpopulation with uniform forward and side scatter properties (ie, size and organelle content) which correlated to those expected of DCs.

Detailed Explanation of Each Method Step in Countercurrent Centrifugal Elutriation Leukapheresis The current patent application discloses a method for rapidly isolating dendritic cells from peripheral blood. In this method, a patient initially undergoes leukapheresis (LP) to isolate white blood cells from other blood cells. Leukapheresis involves extracorporealizing blood continuously from the human donor or patient, using laminar flow properties to separate mononuclear (white) cells and platelets from red cells and plasma. The red cells and plasma were then returned back into the patient. In this fashion, the white cells and platelets can be selectively removed from many liters of patient or donor blood over a several hour period without harming the patient.

Countercurrent Centrifugal Elutriation

The bulk enriched collection of white cells and platelets from leukapheresis was then further fractionated by countercurrent centrifugal elutriation (CCE) (Abrahamsen TG et al. 1991 J. Clin. Apheresis. 6:48–53). Cell samples are placed in a special elutriation rotor. The rotor is then spun at a constant speed of, for example, 3000 rpm. Once the rotor has reached the desired speed, pressurized air is used to control the flow rate of cells. Cells in the elutriator are subjected to simultaneous centrifugation and a washout stream of buffer which is constantly increasing in flow rate. This results in fractional cell separations based largely but not exclusively on differences in cell size.

Our analyses revealed that a subpopulation of dendritic cells was present in all three "traditional" elutriation fractions, though in varying numbers from one collection to another. The dendritic subpopulation typically constituted from one to over 2% of the predominantly lymphocyte fraction; 5–15% of the intermediate fraction, and 2–5% of the monocyte fraction. In addition, a high degree of neutrophil contamination (up to 2/3 of the total cells) was found exclusively in the traditional monocyte fraction. Such neutrophil contamination was more frequently seen during collection from cancer patients than from normal donors. Therefore, following the "traditional" method of elutriation, many dendritic cells were lost in the lymphocyte fraction and, those dendritic cells present in the monocyte fraction were often unusable due to neutrophil contamination.

During our investigations we found, as expected, that cells in the traditional monocyte APC fraction inefficiently presented antigen in several regards:

While generally reliable for restimulating T- lymphocytes already sensitized to "recall" antigens such as tetanus, they were much less efficient in enabling primary sensitization to novel antigens, as well as to tumor antigens in general.

FACS-guided separations indicated that whatever ability the monocyte fraction had to sensitize T lymphocytes to novel antigens was attributable to a small dendritic cell subpopulation.

The monocytes in the monocyte fraction consistently failed to upregulate important costimulatory molecules such as B7.1 when they were cultured in the presence of a variety of test antigens. In contrast, the elutriated dendritic cell subpopulation did upregulate costimulatory molecules in the presence of certain antigens, and such upregulation was accompanied by improved antigen presentation. However, upregulation of costimulatory molecules in the dendritic cell subpopulation did not occur in the presence of most tested antigens, including tumor antigens.

For these reasons, we attempted to improve on the previous dendritic cell isolation methods. The following is an overview of the method for isolating dendritic cells.

Leukapheresis (LP) was driven by "neutrophil-depleting, platelet-rich" software such as Procedure 8 Modification available on the Fenwal™ CS3000 pheresis apparatus (Fenwal, Inc. Round Lake, Ill.). While this product is a preferred software and hardware package that can be used to provide the desired leukapheresis properties, one of ordinary skill in the art will recognize that any similar product that can be programmed to be neutrophil-depleting and platelet-rich will also work in the present invention.

In addition, however, the elutriation (CCE) procedure was modified so that we could elutriate cell subpopulations at a new set of intermediate fractions. This new procedure involved taking additional fractions with a constant rotor speed of 3000 rpm while the buffer flow rate was increasing. Instead of only taking fractions at the traditional flow rates of 140 and 150 cc/min, we obtained cell fractions at 120, 140, 150, 160, 170, 180, 190 and 200 cc/min. Previous investigators had believed that isolating fractions at the higher flow rates would not increase the number if isolated dendritic cells.

We discovered that monocytes and dendritic cells were collectable without neutrophil contamination in newly defined "intermediate" fractions from 150 to 200 (see Table 1). After these new intermediate fractions, a final rotor-off (R/O) fraction was DC poor, monocyte variable, and often highly contaminated by neutrophils. The R/O fraction was easily Coulter analyzed and discarded if contaminated.

When the R/O fraction was highly contaminated, the immediately preceding fractions (200 and sometimes 190) also had a high likelihood of neutrophil contamination. The neutrophil poor fractions—always 150 to 180 and often also 190—were DC enriched and monocyte rich, and were therefore pooled as the "APC" collection. This method of using newly defined intermediate fractions thus enabled easy identification and elimination of neutrophil contaminated fractions, and provided a highly enriched source of DCs.

TABLE 1

Comparison of CCE Fractions in Traditional and New Method

| Fraction | TRADITIONAL METHOD | Fraction | NEW METHOD |
|---|---|---|---|
|  |  | 120* | Essentially pure lymphocytes Non-lymphocyte contaminants can be reduced by extra washes before elutriation and by not overloading the elutriator (maximum 4–5 × 10$^9$ cells/run) This fraction will typically contain less than 0.5% identifiable dendritic cells |
| 140 | Lymphocytes plus contaminant non-lymphocytes from overloading Up to 2% of the fraction by FACS analysis is DCs In absolute numbers, this fraction can contain 25–45% of the total peripheral blood DC concentration in the peripheral blood. | 140* | Large fraction of essentially pure lymphocytes Typically contains less than 0.5% identifiable dendritic cells |
| 150 | Variable discarded fraction, including DCs By FACS analysis, between 15–28% of this fraction are DCs. | 150** | Lymphocytes plus first DC-rich fraction DCs ~5–10% of this fraction |
|  |  | 160** | DC-richest fraction, rest monocytes DCs ~15–25% of this fraction |
|  |  | 170** | DC-richest fraction, rest monocytes DCs ~15–25% of this fraction |
|  |  | 180** | DC-rich fraction, rest monocytes DCs ~10–15% of this fraction |
|  |  | 190** | Monocyte fraction, variably DC rich DCs ~5–10% of this fraction |

TABLE 1-continued

Comparison of CCE Fractions in Traditional and New Method

| Fraction | TRADITIONAL METHOD | Fraction | NEW METHOD |
|---|---|---|---|
| | | 200 | Monocyte fraction, rarely DC rich Sometimes contaminated by neutrophils DCs less than 5% of this fraction |
| R/O | Monocyte fraction less than 5% of total DC population, often largely neutrophil contaminated | R/O | Monocyte fraction Sometimes neutrophil contamination DCs typically less than 2% of fraction |

*Usually pooled as "lymphocyte fraction"
**Usually pooled as "APC" fraction

As shown in Table 1, traditional CCE methods resulted in loss of DCs into the earlier lymphocyte (140) and intermediate (150) fraction despite the fact that DCs are larger in size than lymphocytes and technically should not be eluted in great numbers until after the 150 fraction. This is one reason why this problem has persisted in the art until our improvement. Because the traditional lymphocyte (140) fraction constituted over 5/7 of the total elutriated cells products, a very small percentage of dendritic cells in the fraction would constitute between 25–45% of the total dendritic cell population in the peripheral blood.

We believe that specific factors contributed to premature dumping of DCs in the elutriation process, including carryover of plasma proteins from LP into CCE, apparently altering cell sedimentation rates. In addition, it seems that in cancer patients carryover tumor-related blood proteins from LP into CCE. Finally, addition of certain chemicals such as EDTA to the buffer during elutriation appears to negatively effect isolation efficiencies. To prevent these factors from impairing elutriation, we have introduced a washing step: following LP (leukapheresis), the cells are centrifuged, resuspended in a cold citrate buffer solution, and washed thoroughly to reduce the carryover of plasma, tumor-related proteins, calcium, etc. Subsequently, the cells are resuspended in EDTA-free, $Ca^{++}/Mg^{++}$ free Hanks' balanced salt solution (HBSS) before being subjected to elutriation. With this corrected technique, a small initial enrichment of DCs begins to appear at fraction 150 with peak DC elutriation reliably occurring between fractions 155 and 180, and is largely completed by fraction 190. This improvement would not have been expected upon addition of a washing step following leukapheresis.

Maintaining Elutriated Cells on Ice

We have also identified that there is a major loss of cells during elutriation due to adhesion of cells to plastic bags during collection. This is probably exacerbated when the cells are kept in the bag for extended periods prior to processing. We have ascertained that this adhesion is temperature dependent, and lowering the temperature during collection typically doubles the yield of the monocyte/DC fractions. Elutriation has therefore been modified to reduce the collection temperature to 4° by keeping the collection bags on ice and partially prefilling them with chilled buffer. This markedly improves yields and does not detectably impair function. Since cells are normally cryopreserved after elutriation, they are maintained at this low temperature until the cryopreservation process.

FACS Analysis to Monitor Quality of Elutriation

Quality control of APC collection and confirmation of their successful activation in culture is dependent upon a simultaneous multi-color FACS analysis technique we have developed to monitor both monocytes and the dendritic cell subpopulation as well as possible contaminant T lymphocytes. It is based upon the fact that DCs have absent or low expression of the following markers: CD3 (T cell); CD14 (monocyte); CD16,56,57 (NK/LAK cells); CD 19, 20 (B cells). At the same time, DCs do express large quantities of HLA-DR, significant HLA-DQ and B7.2 (but little or no B7.1) at the time they are circulating in the blood (in addition they express Leu M7 and M9, myeloid markers which are also expressed by monocytes and neutrophils). When combined with a third color reagent for analysis of dead cells, propridium iodide (PI), it is possible to make positive identification of all cell subpopulations (see table 2):

TABLE 2

FACS analysis of fresh peripheral cell subpopulations

| | Color #1 Cocktail 3/14/16/19/20/56/57 | Color #2 HLA-DR | Color #3 PI |
|---|---|---|---|
| Live Dendritic cells | Negative (or low CD14) | Positive | Negative |
| Live Monocytes | Positive | Positive | Negative |
| Live Neutrophils | Negative (or low CD14) | Negative | Negative |
| Dead cells | Variable | Variable | Positive |

Additional markers can be substituted for additional analysis:

Color #1: CD3 alone, CD14 alone, etc; Leu M7 or Leu M9; anti-Class I, etc

Color #2: HLA-Dq, B7.1, B7.2, CD25 (IL2r), ICAM, LFA-3, etc.

The goal of FACS analysis at the time of collection is to confirm that the DCs are enriched in the expected fractions (150–190), to monitor neutrophil contamination, and to make sure that appropriate markers are expressed. This rapid bulk collection of enriched DCs from human peripheral blood, suitable for clinical applications, is absolutely dependent on the analytic FACS technique described above for quality control. If need be, mature DCs can be immediately separated from monocytes at this point by fluorescent sorting for "cocktail negative" cells. We do not, however, routinely separate DCs from monocytes because, as will be detailed below, the monocytes themselves are still capable of differentiating into DCs or functional DC-like cells in culture.

Once collected, the DC rich/monocyte APC fractions (usually 150 through 190) can be pooled and cryopreserved for future use, or immediately placed in short term culture. We have defined new and essential culture conditions for optimal activation of and antigen processing by these APCs. The goals are:

to enable optimal processing of added proteins or uptake of pulsed peptides optimal and controlled upregulation of essential costimulatory and presenting molecules on DCs such as B7.1, B7.2 and HLA-DR and HLA-DQ.

conversion of the large monocyte population to an activated DC-like phenotype so that they also can participate in effective antigen processing and presentation. Example 1 below describes the isolation of dendritic cells from normal humans and humans with colon cancer.

As used herein the terms upregulate, downregulate, and de novo express mean that the cell type exposed to the agent which induces the cell surface expression of an activated myeloid dendritic cell phenotype increases, decreases, or causes expression of a cell surface marker not previously expressed for the relevant cell surface marker relative to a control cell of the same cell type which has not been exposed to the agent.

EXAMPLE 1

Two patients were hooked up to Fenwal™ CS-3000 leukapheresis apparatus' running a Procedure 8 modification software program. Patient #1 had been previously diagnosed with colon cancer, and Patient #2 was a normal control. The Fenwal™ apparatus was configured to isolate a sample of neutrophil-depleted, platelet-rich cells from each patients' peripheral blood. After 3–5 hours of leukaphereis, the isolated blood cells from each patient were quickly spun down in a centrifuge and then rinsed in citrate buffer to remove any excess plasma, tumor related proteins or calcium.

Following the citrate buffer rinse, the cells were resuspended in EDTA-free, $Ca^{++}/Mg^{++}$ HBSS. The isolated cells from each patient were then subject to elutriation on a Beckman™ JE-6B elutriation rotor. Once reaching a speed of 3000 rpm, $5 \times 10^9$ cells were elutriated by pressurized air at buffer flow rates of 120, 140, 150, 160, 170, 180, 190 and 200 cc/minute.

Each fraction from both patients were immediately placed on ice to prevent cell adherence to the plastic walls of the collection vials. We coulter counted each of the fractions and discarded the r/o fraction because it had greater than a 10% contamination of neutrophils. The 150, 160, 170, 180 and 190 cc/min fractions from Patient #1 and Patient #2 were pooled then subject to calcium ionophore. The pooled fractions from each patient were divided in half, with one half being activated by 500 ng of calcium ionophore A23187 (Sigma), and one half being inactivated. From our previous experiments, we expected that the calcium ionophore treated cells would have a much higher number of dendritic cells due to conversion of monocytes to DCs. Prior to FACS analysis, we activated Patient #1's pooled fractions by incubating both the untreated and calcium ionophore treated cells for 40 hours in the presence of an autologous tumor cell lysate (the patients own tumor cells). Similarly, we activated Patient #2's pooled fractions by incubating both the untreated and calcium ionophore treated cells in the presence of keyhole limpet hemocyanin (KLH) for 40 hours.

In each of the FACS plots, the vertical (Y) axis showed staining for a cocktail of CD3, CD14, CD20 and CD56 surface antigens. The vast majority of cells stained in the pooled fractions were expected to be CD14+(ie: monocytes). The horizontal (X) axis of the FACS plot illustrated staining for DR, B7.1 or B72 surface antigens. Our results of the FACS analysis were as follows:

Normal Donor (NO calcium ionophore treatment)

The vast majority of cells in this fraction remained CD14+indicating that they remained monocytes. However, a subset of the cocktail negative (dendritic) cells showed marked upregulation of HLA-DR, B7.1 and B7.2.

Normal Donor (WITH calcium ionophore treatment)

The vast majority of these cells was now cocktail negative (dendritic) and markedly upregulated for HLA-DR, B7.1 and B7.2. This matched a dendritic cell phenotype indicating that a number of the monocytes had converted over to dendritic cells.

Colon Cancer Pt. (NO calcium ionophore treatment)

The vast majority of these cells remained cocktail positive, with a subset of negative (dendritic) cells showing modest upregulation of HLA-DR, and B7.2, but only a little upregulation of B7.1.

Colon Cancer Pt. (WITH calcium ionophore treatment)

The vast majority of cells were now converted to cocktail negative indicating that they had become dendritic cells. There was a marked upregulation of HLA-DR and B7.2. There was also a substantial but less uniform upregulation of B7.1.

This experiment demonstrated that calcium ionophore treatment increased the yield of activated dendritic cells by many times over untreated cell fractions. We are able to obtain up to $1 \times 10^9$ dendritic cells using this technique from a single peripheral blood leukapheresis. This is an increase of more than 100 fold over previous dendritic cell isolation methods. The use of calcium ionophore to convert monocytes to dendritic cells can therefore provide a very valuable tool for investigators and clinicians that require large numbers of dendritic cells for a clinical treatment.

As discussed above, populations of activated dendritic cells isolated by the method of the present invention can be easily re-introduced into a patient to help augment a weak or dysfunctional immune system.

Example 2 below describes the preparation of human peripheral blood mononuclear cells (PBMC).

EXAMPLE 2

Twelve healthy volunteers and six cancer patients (three with melanoma, three with colon cancer) provided informed consent to undergo the National Cancer Institute's leukapheresis and countercurrent centrifugal elutriation (CCE) protocol for quantitative collection of peripheral blood lymphocytes and myeloid origin mononuclear cells (MOMC). All collection steps were performed with pyrogen-free reagents. Each donor was initially leukapheresed 5–7 liters whole blood on a Fenwal CS3000 blood cell separator programmed for minimized neutrophil contamination. The leukapheresis concentrate was acquired in small volume collection chambers to reduce platelet contamination. This concentrate typically yielded $4-10 \times 10^9$ PBMC, which were immediately washed in a large volume of citrate-anticoagulated normal saline to remove contaminant platelets and plasma.

The washed cells were resuspended in $Ca^{++}/Mg^{++}$ free, pyrogen-free HBSS (Bio Whittaker, Walkersville, Md.) and elutriated using a Model J-6M centrifuge equipped with a JE-5.0 elutriation rotor operating at 1725 g and 20° C. (Beckman Instruments, Palo Alto, Calif.). (Cohen, P. A. et al. 1993. *J. Immunother.* 14:242; Abrahamsen, T. G. et al. 1991. *J. Clin. Apheresis.* 6:48). Cells were loaded at 120 cc/minute flow rate, then fractions collected using stepwise flow rates ranging from 120 to 200 cc/minute to obtain lymphocyte-rich (120 and 140 cc/minute), transitional (150 cc/minute) and MOMC-rich (170, 190, 200 cc/minute) fractions. A final MOMC-rich fraction was collected at zero rpm (rotor off, or R/O fraction). Fractions were accumulated in Life Cell tissue culture vessels (Baxter Health Care, Deerfield, Ill.) on ice to inhibit cellular adherence. Lymphocyte-rich fractions (120–140) but not MOMC-rich fractions were further purified with density gradient centrifugation using pyrogen-free Ficoll-Hypaque (Bio whittaker) to remove red blood cells.

Despite efforts to minimize neutrophil contamination, late elutriation fractions (R/O and rarely 200 cc/minute) from cancer patients frequently contained a preponderance of neutrophils; when this occurred these fractions were discarded. Occasional minor (<5%) basophil contamination was observed in 170 cc/minute MOMC-rich fractions.

Elutriated fractions were either immediately utilized in experiments or cryopreserved in 10% DMSO, 90% pooled heat inactivated human AB recalcified plasma (Sigma Chemical, St. Louis, Mo.) for future thaw and use. Exposure to fetal bovine serum (FBS) was avoided in all experiments.

Individual elutriation fractions collected as described above at increasing buffer flow rates were analyzed by FACS for the presence of strongly HLA-DR$^{pos}$ cells which simultaneously lacked T cell, B cell, natural killer (NK) cell and monocyte markers, the putative phenotype of immature dendritic cells (iDC). (Freudenthal, P. S. and R. M. Steinman. 1990. *Proc. Natl. Acad. Sci. U. S. A.* 87:7698; Peters, J. H., et al. 1996. *Immunol. Today* 17:273; Nijman, H. W., et al. 1995. *J. Exp. Med.* 182:163). This was accomplished by staining cells simultaneously with PE-conjugated anti-HLA-DR and a cocktail (COCK) of FITC-conjugated anti-CD3, anti-CD20, anti-CD57 and anti-CD14. The percentage of cells in each fraction expressing this iDC phenotype correlated closely to the percentage of cells which were CD33$^{pos}$, CD14$^{neg/dim}$ (i.e., of myeloid origin with low CD14 expression, not shown).

Example 3 below describes the FACS analysis of elutriated cells.

EXAMPLE 3

Elutriated fraction cells were analyzed before and/or after in vitro culture by fluorescent multicolor flow cytometry (FACScan, Becton-Dickinson, Mountain View, Calif.). Cells were stained at 4° C. using Ca$^{++}$/Mg$^{++}$-free HBSS with 0.2% BSA and 0.1% sodium azide as a diluent/wash FACS buffer. Cells were incubated with 1 mg/ml human IgG (Sigma Chemical, St. Louis, Mo.) for 10 minutes to block FcR, then, in most cases, double stained with PE- and FITC-conjugated Ab for 30 minutes. When unconjugated Ab were used instead (mouse anti-human CD83 or HLA-DQ) cells were first stained with the unconjugated reagent or subclass matched control Ab, washed, counterstained with PE-conjugated goat anti-mouse IgG, washed, blocked with 10% heat inactivated mouse serum (Harlan, Indianapolis, Ind.), then stained with FITC-conjugated Ab. After wash with cold FACS buffer, cells were resuspended and propridium iodide (PI) added to distinguish viable from non-viable cells, then three color analysis was immediately performed on unfixed cells using a 5 watt Argon laser emitting 200 mW of 488 nm light. Simultaneous measurement of FITC, PE, and PI emissions was performed using 530, 575 and 650 filters with acquisition in logarithmic mode. Unviable cells were clearly delineated in FL3 (650 nm) vs forward scatter display, and were excluded from final analysis.

Fractions of peripheral blood mononuclear cells (PMBC) prepared as described above were analysed to determine the distribution of immature dendritic cells using the above described FACS analysis. The results of the analysis are shown in FIGS. 1A and 1B, in which the cells which were present in each of the elutriation fractions, were stained with PE-conjugated mouse anti-human HLA-DR and a cocktail (COCK) of FITCconjugated mouse anti-human CD3, CD14, CD20 and CD57 to determine the percentage of immature dendritic cells present in each fraction. In FIG. 1A, the abscissa shows elutriation rate in cc/min at the time of each fraction collection; ">190" designates either pooled 200+ R/O fractions or the 200 fraction alone when the RIO fraction was discarded. In FIG. 1A, the ordinate shows the percentage of cells in each fraction which were HLA-DR$^{pos}$, COCK$^{neg/dim}$ (neg/dim as used herein meaning that there was little or no expression of the marker or markers analyzed). This correlated closely to the fraction of cells which were CD33$^{pos}$CD14$^{neg/dim}$.

As shown in FIG. 1A, only a marginally detectable subpopulation of cells (<1.0%) displayed the iDC staining pattern in early, lymphocyte-predominant elutriation fractions (120–140 cc/minute flow rates). However, a larger percentage of cells (up to 28%) displayed this pattern in subsequent fractions (FIG. 1A). 150 cc/minute fractions were typically a transitional mixture of lymphocytes and CD33$^{pos}$ myeloid origin mononuclear cells (MOMC), while later fractions (170, 190 and 200 cc/minute, and R/O) consisted predominantly of MOMC.

FIG. 1B shows the percentage of the total leukapheresed cells with the surface phenotype of immature dendritic cells (iDC) recovered in each elutriation fraction from four representative donors. The calculated content of each donor's pooled MOMC-rich fractions (170+190+>190) is also displayed. As shown in FIG. 1B, maximum proportions of cells with an iDC phenotype usually appeared at 150–170 cc/minute collection, but relatively large absolute numbers of cells with this staining pattern were also present at still faster collection rates. For this reason, an individual donor's MOMCpredominant fractions were often combined prior to culture, cryopreservation and/or further purification by FACS or superparamagnetic microbeading.

Example 4 below describes the enrichment of enrichment of CD14$^{neg}$ myeloid origin mononuclear cells (MOMC) (immature dendritic cells) by FACS.

EXAMPLE 4

CD14$^{neg}$ immature dendritic cells (iDC) were sorted by flow cytometry (Becton Dickinson FACStar) from elutriated MOMC prior to culture using a negative selection technique. The threshold was set on forward angle light scatter and the sorting gate was set on fluorescence. Thawed or fresh elutriation fractions were stained with a cocktail of FITC-conjugated azide-free anti-human CD14, CD3, CD20 and CD56 to identify monocytes and contaminant T, B, and NK cells. Strongly and dimly staining sorted cells were discarded; nonstaining cells were collected and either immediately analyzed or placed in culture.

Further analysis of combined MOMC-predominant elutriation factors was conducted as described in Example 5 below.

EXAMPLE 5

Analysis of Combined MOMC-Predominant Elutriation Fractions

Pooled MOMC-predominant fractions obtained from a representative healthy volunteer by combined leukapheresis/CCE as described above were evaluated prior to culture for expression of cell surface molecules by multicolor flow cytometry.

The results of the evaluation are shown in FIG. 2. Labels on horizontal and vertical axis indicate the parameter evaluated. COCKTAIL (FITC-COCK) designates a cocktail of FITC-conjugated mouse anti-human CD3, CD14, CD20 and CD57. In FIG. 2A, cells were stained with mouse IgG subclass matched phycoerythrin (PE) and FITC conjugated control Ab. In FIG. 2B, cells were stained with FITC-conjugated mouse anti-human CD14 vs PE-conjugated mouse anti-human CD33. In FIG. 2C, cells were stained with FITC-COCK vs PE-conjugated mouse anti-human CD33.

Figure 2B:
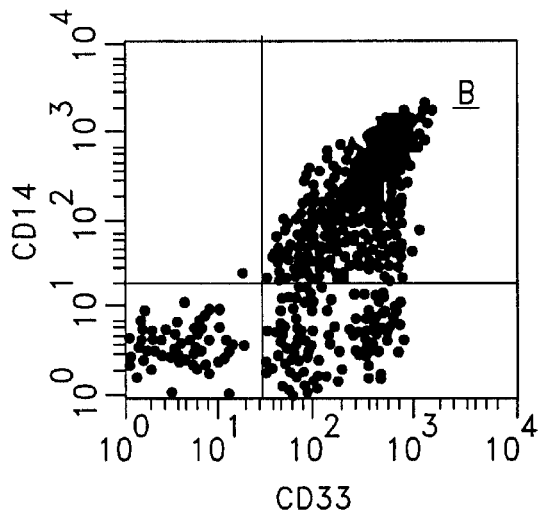
FIG. 2B is a FACS analysis of pooled MOMC stained with FITC-conjugated mouse anti-human CD14 vs PE-conjugated mouse anti-human CD33.
Figure 2C:
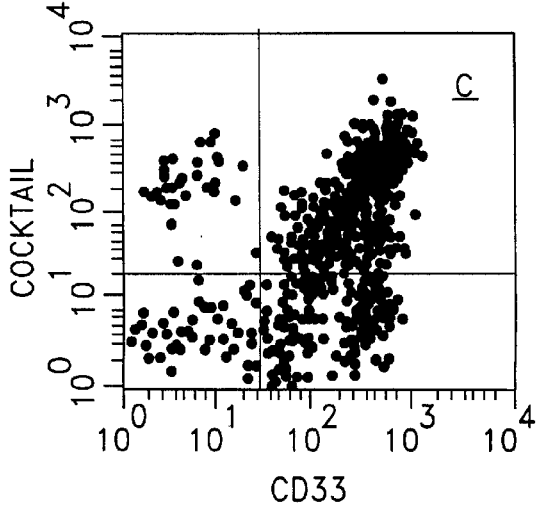
FIG. 2C, is a FACS analysis of pooled MOMC stained with FITC-COCK vs PE-conjugated mouse anti-human CD33.

As shown in FIGS. 2A and 2B, combined MOMC-predominant elutriation fractions were typically composed almost exclusively (>98%) of CD33$^{pos}$ cells, of which 88–90% displayed a CD14$^{pos}$, CD33$^{pos}$ monocyte phenotype and 7–10% displayed a CD14$^{neg/dim}$, CD33$^{pos}$ iDC phenotype. Trace numbers of contaminant CD33$^{neg}$ cells (<2% of total cells) were all CD14$^{neg}$ (FIG. 2B) and included both COCK$^{neg}$ and COCK$^{pos}$ cells (FIG. 2C), the latter proving to be contaminant lymphocytes. Greater than 98% of all COCK$^{pos}$ cells could therefore be assigned a CD14$^{pos}$, CD33$^{pos}$ monocyte phenotype, while greater than 90% of COCK$^{neg/dim}$ cells could be assigned a CD14$^{neg/dim}$, CD33$^{pos}$ iDC phenotype (FIGS. 2B and 2C). In many analyses FITC-COCK was used rather than FITC-anti-CD14 to distinguish monocytes from iDC, thereby forcing contaminant lymphocytes to be displayed as a minor contaminant of the large monocyte subpopulation rather than as an iDC contaminant.

Figure 2D:
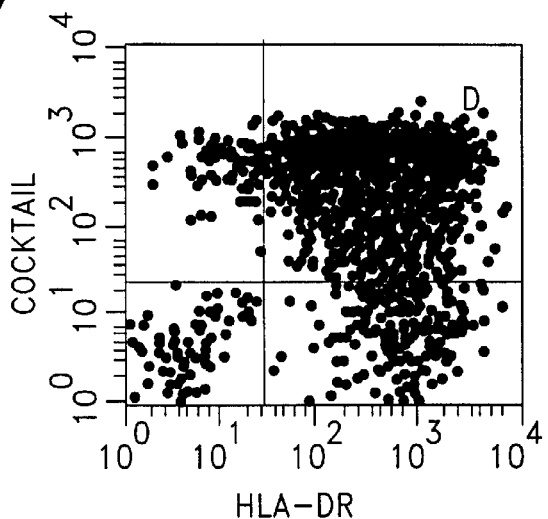
FIG. 2D is a FACS analysis of pooled MOMC stained with stained with FITC-anti-CD14 vs PE-mouse anti-human HLA-DR.
Figure 2E:
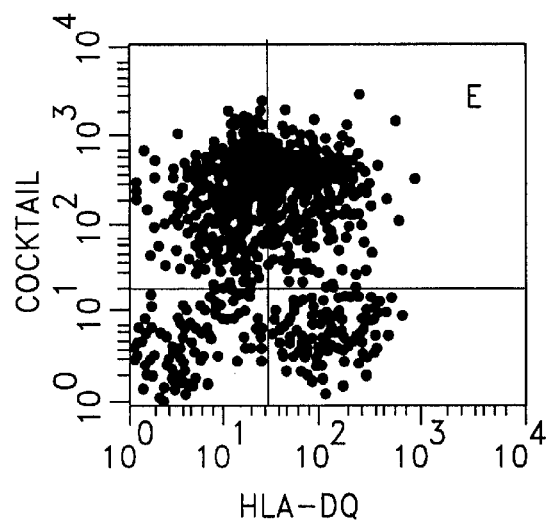
FIG. 2E is a FACS analysis of pooled MOMC stained with unconjugated mouse anti-human monomorphic HLA-DQ, counterstained with PE-conjugated goat anti-mouse IgG (GAM-PE), blocked with 10% mouse serum, then stained with FITC-COCK.
Figure 2F:
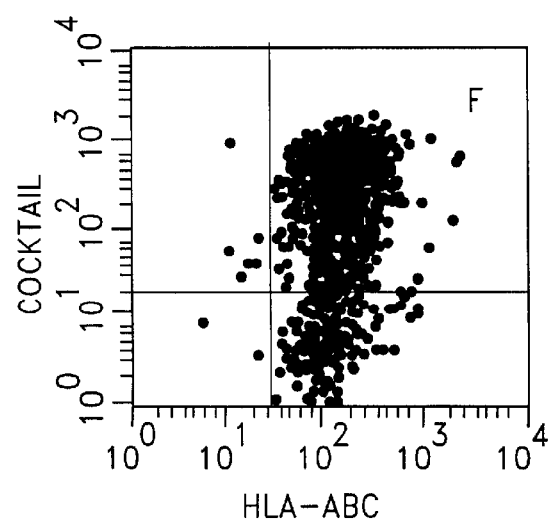
FIG. 2F is a FACS analysis of pooled MOMC stained with FITC-COCK vs PE-conjugated mouse anti-human monomorphic HLA-ABC.
Figure 2G:
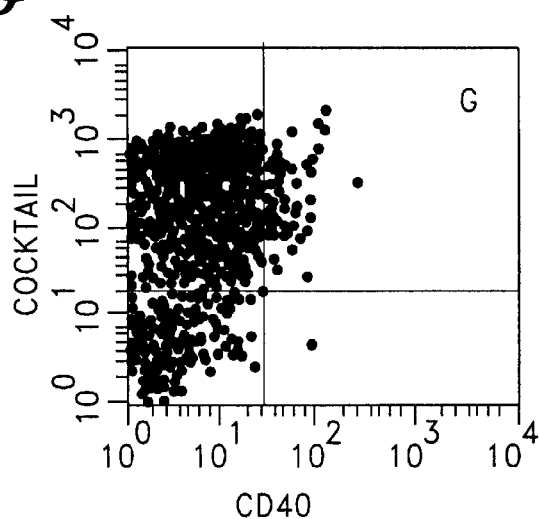
FIG. 2G is a FACS analysis of pooled MOMC stained with stained with FITC-COCK vs PE-mouse anti-human CD40.
Figure 2H:
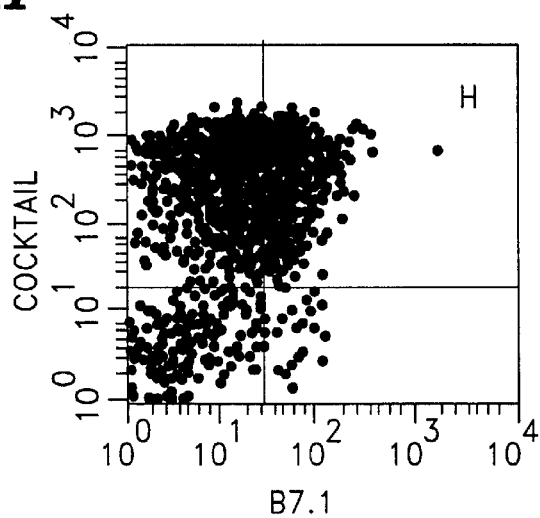
FIG. 2H is a FACS analysis of pooled MOMC stained with FITC-COCK vs PE-mouse anti-human B7.1 (CD80).
Figure 2I:
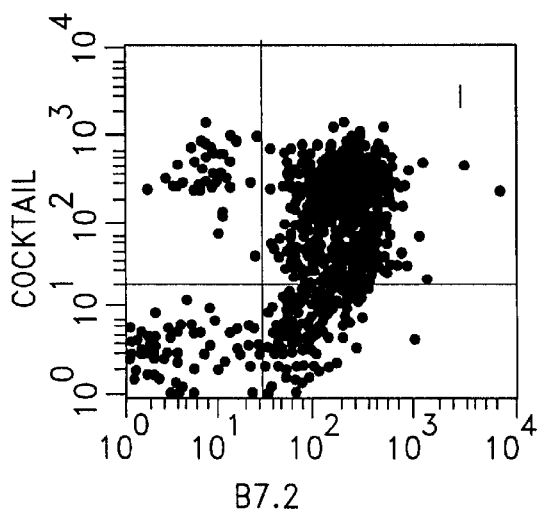
FIG. 2I is a FACS analysis of pooled MOMC stained with FITC-COCK vs PE-mouse anti-human B7.2 (CD86).
Figure 2J:
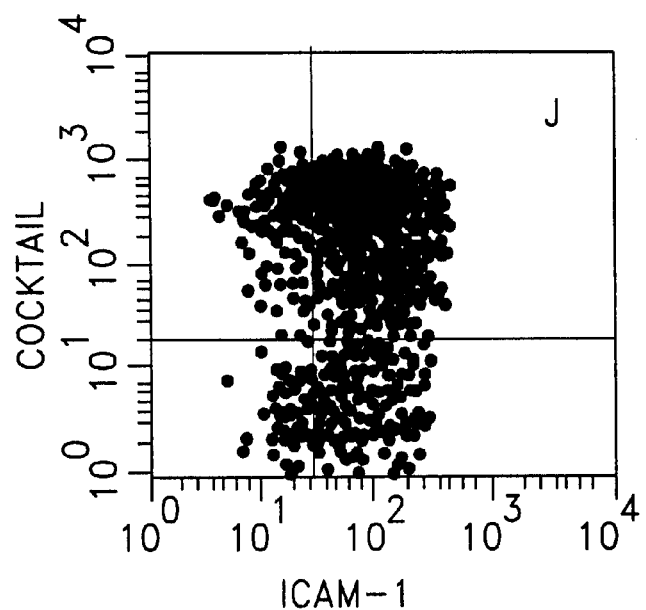
FIG. 2J is a FACS analysis of pooled MOMC stained with FITC-COCK vs PE-mouse anti-human ICAM-1 (CD54).
Figure 2K:
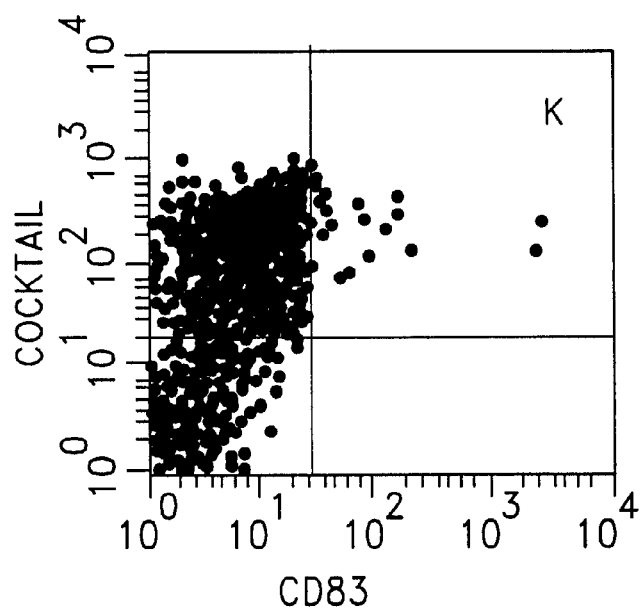
FIG. 2K is a FACS analysis of pooled MOMC stained with stained with unconjugated mouse anti-human CD83 (HB15a), counterstained with PE-conjugated goat anti-mouse IgG, blocked with 10% MS, then stained with FITC-COCK.

The pattern of cell surface markers present in uncultured monocyte fractions was also assessed. The results are shown in FIGS. 2D–2K. In FIG. 2D, cells were stained with FITC-anti-CD14 vs PE-mouse anti-human HLA-DR. In FIG. 2E, cells were stained with unconjugated mouse anti-human monomorphic HLA-DQ, counterstained with PE-conjugated goat anti-mouse IgG (GAM-PE), blocked with 10% mouse serum, then stained with FITC-COCK. In FIG. 2F, cells were stained with FITC-COCK vs PE-conjugated mouse anti-human monomorphic HLA-ABC. In FIG. 2G, cells were stained with FITC-COCK vs PE-mouse anti-human CD40. In FIG. 2H, cells were stained with FITC-COCK vs PE-mouse anti-human B7.1 (CD80). In FIG. 2I, cells were stained with FITC-COCK vs PE-mouse anti-human B7.2 (CD86). In FIG. 2J, cells were stained with FITC-COCK vs PE-mouse anti-human ICAM-1 (CD54). In FIG. 2K, cells were stained with unconjugated mouse anti-human CD83 (HB15a), counterstained with PE-conjugated goat anti-mouse IgG, blocked with 10% MS, then stained with FITC-COCK. Subclass matched unconjugated mouse IgG controls for FIG. 2E and FIG. 2K counterstained with GAM-PE resulted in background levels of fluorescent intensity identical to those seen in FIG. 2A.

As shown in FIGS. 2D and 2F uncultured CD14$^{neg}$, CD14$^{dim}$ and CD14$^{pos}$ subpopulations displayed uniformly high surface expression of MHC Class I and HLA-DR, with several intensities of HLA-DR staining apparent in the CD14$^{pos}$ subpopulation. HLA-DQ expression was heterogeneous but present, with a subset of strongly staining CD14$^{neg}$ cells, as shown in FIG. 2E. Uncultured MOMC did not detectably express the DC-associated activation marker CD83 identified by mAb HB-15a (FIG. 2K) (mAb HB-15a was obtained from Dr. Thomas Tedder (Duke University Medical Center, Durham, N.C.). Each subpopulation had similar initial expression of costimulatory molecules, with generally strong expression of surface B7.2 (CD86), modest to strong expression of ICAM-1 (CD54), and undetectable B7.1 (CD80) (FIG. 2H–2J). CD40 expression was absent or dim (FIG. 1G). This profile was observed whether MOMC were obtained from healthy volunteers or from patients with malignancies. In addition, CD14$^{neg}$ cells sorted by FACS were indistinguishable ultrastructurally from predominantly (88–90%) CD14$^{pos}$ MOMC.

When the ultrastructural characteristics of uncultured MOMC were examined using electron microscopy, a wide range of membrane-bound granule and Golgi content was observed among cells in each group. The majority of cells from both a nonsorted pool of MOMC (>90% CD14$^{pos}$ monocytes) and CD14$^{neg}$ cells isolated from MOMC by FACS (90% purity) closely resembled one another and had dispersed short cytoplasmic processes. Long processes were rare. The nuclei were central, clefted or bilobed, and the cytoplasm was scant to moderate. Many cells had a well developed Golgi system, as well as a moderate complement of mitochondria and endoplasmic reticulum.

The above combined leukapheresis and CCE procedures have enabled nearly quantitative isolation of circulating lymphocytes and CD33$^{pos}$ MOMC from the peripheral blood of all studied individuals. With phereses in the 7–10 liter range, 2–4×10$^9$ lymphocytes and 1–3×10$^9$ CD33$^{pos}$ MOMC are readily isolated from individual donors on a repetitive basis, and many functional characteristics of these cells are demonstrably retained after cryopreservation and subsequent thaw, including all those described in the present report. Large absolute numbers of iDC are present as a less than 1% subpopulation in lymphocyte-predominant elutriation fractions, and these may be identical to iDC isolated by others from lymphocyte fractions using Percoll gradients. Mehta-Damani, A., S. Markowicz, and E. G. Engleman. 1995. Generation of antigen-specific CD4+ T cell lines from naive precursors. Eur. J. Immunol. 25:1206; Mehta-Damani, A., S. Markowicz, and E. G. Engleman. 1994. Generation of antigen-specific CD8+ CTLs from naive precursors. J. Immunol. 153:996). Much larger proportions of iDC (3–28%) are present in 170–200 cc/ml MOMC-predominant elutriation fractions, the remainder of cells in these fractions largely consisting of CD14$^{pos}$ monocytes. Although iDC are too minute a component to allow accurate direct FACS analysis in unfractionated whole blood, they are sufficiently conspicuous in MOMC fractions to permit tentative FACS monitoring without further isolation from CD14$^{pos}$ monocytes.

MOMC collected by this method are in a minimally manipulated state, not having contacted density gradient media, adherence substrates, FBS, and/or pyrogen prior to elective culture and Ag exposure; in addition, ex vivo contact with stagnant platelets, neutrophils and donor plasma has been minimized. The ultrastructural and immunophenotypic profiles of uncultured, elutriated iDC and monocytes are very similar, except for CD14 expression. The same immunophenotypic profile was detected on CD14$^{pos}$ cells when heparinized whole blood is collected on ice and analyzed within 30 minutes by flow cytometry, confirming that this is the constituitively expressed phenotype of circulating monocytes; others have also reported constitutive B7.2 but not B7.1 expression on resting monocytes and iDC (Fujihara, M., T. A. et al. 1996. Blood 87:2386; McLellan, A. D., et al. 1995. Eur. J Immunol. 25:2064; Takamizawa, M., et al. 1997. J. Immunol. 158:2134; Weissman, D., et al. 1995. J. Immunol. 155:4111).

The effects of various culture conditions and agents on the pattern of cell surface marker expression were analyzed as described below.

II. Use of Calcium Ionophore to Convert Monocytes into Activated Dendritic Cells We have discovered that a new and useful method exists for upregulating (activating) dendritic cells and converting monocytes to an activated dendritic cell phenotype. This method involves our discovery that addition of calcium ionophore to the culture media convert monocytes into activated dendritic cells. Adding the calcium ionophores A23187 or ionomycin, for example, at the beginning of a 24–48 hr culture period resulted in uniform activation and dendritic cell phenotypic conversion of the pooled "monocyte plus DC" fractions. Treatment of monocytes with the calcium ionophore A23187 rapidly produced the following pattern of cell surface marker expression which is consistent with the induction of a phenotype characteristic of activated myeloid dendritic cells.

Monocytes treated with calcium ionophore exhibited a marked downregulation of cell surface CD14 within 18 hours of treatment initiation. This effect of calcium ionophore was observed in all tested medium, including medium with 10% human serum.

In addition monocytes treated with calcium ionophore exhibited a de novo and essentially uniform expression of the dendritic cell-associated activation marker CD83 within 18 hours of treatment initiation (Zhou and Tedder, *Proc. Natl. Acad. Sci. U. S. A.* 93:2588, 1996). Expression of this marker frequently declines after 18 hours.

Monocytes treated with calcium ionophore also exhibited a marked upregulation of B7.2 (CD86) within 18 hours of calcium ionophore treatment initiation which occurs in all donors, even those who display sluggish B7.1 upregulation, as discussed below. Variable levels of de novo expression of B7.1 (CD80) were observed within 18 hours of initiation of calcium ionophore treatment. B7.1 was typically highly detectable but not uniformly expressed at 18 hours. Rarely an occasional donor's monocytes show negligible expression of B7.1 at 18 hours unless adjunct enhancing agents such as amphotericin B, LPS (endotoxin), rhGM-CSF or rhIFN-gamma are also present.

Modest upregulation of CD40 which becames more uniform by 40 hours of treatment was also observed when monocytes were treated with calcium ionophore.

The above described pattern of cell surface marker expression observed when monocytes are treated with calcium ionophores is characteristic of the pattern of cell surface marker expression seen on activated myeloid dendritic cells.

In addition to having a cell surface marker expression pattern characteristic of activated myeloid dendritic cells, calcium ionophore treated monocytes had the morphological characteristics of activated myeloid dendritic cells. Calcium ionophore treated monocytes appeared much more vacuolated on light microscopy within 20–40 hours of calcium ionophore treatment, and electron microscopy revealed calcium ionophore treated monocytes to have markedly increased endoplasmic reticulum, lysosomal and Golgi content. Calcium ionophore treated monocytes which were transferred to polylysine coated glass slides after 40 hours maintained a small rounded appearance and developed multiple short or long dendritic processes extending from all surfaces in contact with the glass, with many cells having a uniform halo of spike-like processes. This tendency to develop long dendritic processes increased markedly between 40 and 96 hours in culture.

As described in Examples 6,7, and 8 below, calcium ionophore treated monocytes also developed the ability to effectively present antigens, a functional characteristic of activated myeloid dendritic cells.

EXAMPLE 6

Calcium ionophore treated monocytes developed T cell sensitizing capacity indistinguishable from purified dendritic cells.

Uncultured monocytes and DC were each purified from elutriation fractions using Miltenyi microsuperparamagnetic beads; monocytes were positively selected based on CD14 expression, while dendritic cells were negatively selected based on low CD14 expression, then positively selected based on CD33 (myeloid marker) expression. Each isolated fraction was cultured for 40 hours either in medium alone or in ionophore A23187 750 ng/ml, then harvested and either FACS analyzed or microcultured with freshly prepared allogeneic T lymphocytes. Graded numbers of the cultured monocytes or dendritic cells were added to fixed numbers of T cells to compare their antigen-presenting ability. Four days later the microcultures were pulsed with $^3$H-dTr and harvested 18 hours later.

Figure 3B:
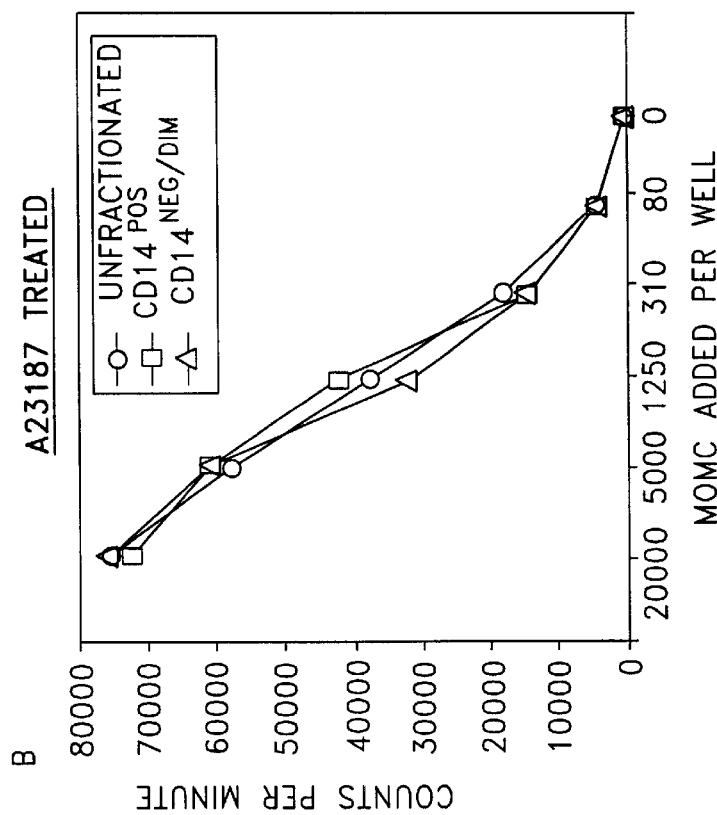
FIG. 3B shows the T cell allosensitization potency of MOMC groups treated with A23187 ("A23187 Treated").
Figure 3A:
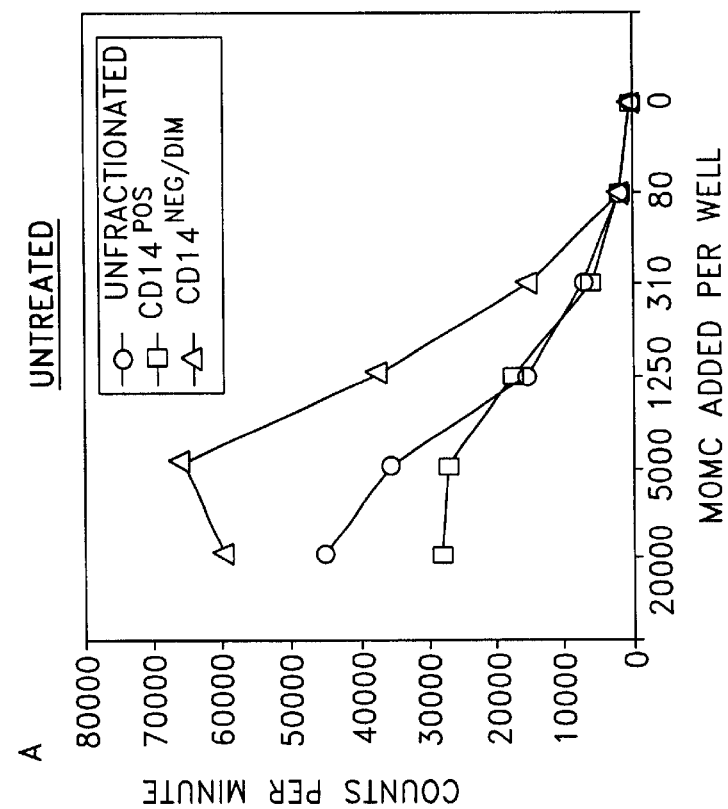
FIG. 3A shows the T cell allosensitization potency of MOMC groups not treated with A23187 ("Untreated").

The results are shown in FIG. 3. SEM of triplicate wells are displayed as error bars. Graphs A and B are plotted on the same scale to enable cross-comparison. FIG. 3A: T cell allosensitization potency of MOMC groups not treated with A23187 ("Untreated"); FIG. 3B: T cell allosensitization potency of MOMC groups treated with A23187 ("A23187 Treated"). All MOMC groups cultured without T cells generated <200 cpm (not shown). Results shown are representative of three separate experiments.

During 40 hours in culture without calcium ionophore purified dendritic cells showed a variable but overall marked tendency to upregulate markers such as B7.1, B7.2, HLA-DR, CD40 and CD83, whereas this was extremely uncommon among purified monocytes not treated with calcium ionophore.

In contrast, calcium ionophore caused upregulation of B7.1, B7.2, ICAM-1., HLA-DR, HLA-ABC, CD40, and CD83 in both monocyte and DC cultures, ultimately rendering the levels of expression on most monocytes and most DC indistinguishable from one another In the absence of calcium ionophore treatment, on a graded numbers basis, purified DC were more efficient than purified monocytes or mixed populations in achieving allostimulation.

In contrast, while calcium ionophore-treated purified DC showed only a modest increase in T cell sensitizing efficiency, calcium ionophore-treated purified monocytes showed a more marked enhancement. In fact, after calcium ionophore treatment, the efficiency of dendritic cells, monocytes or mixed populations were indistinguishable from one another.

Thus, calcium ionophore treatment enhances antigen-presenting efficiency of both monocytes and dendritic cells which correlates well to its enhancing effects on costimulatory molecule and MHC expression in both these subpopulations; during calcium ionophore treatment both monocytes and dendritic cells trend towards maximal development of an activated dendritic cell phenotype.

As discussed in Example 7 below, the antigen presenting ability of monocytes treated with calcium ionophores was superior to that obtained when monocytes were treated with rhGM-CSF plus rhIL4.

EXAMPLE 7

Monocyte rich elutriation fractions were cultured for 40 hours with either no additives, ionophore A23187 750 ng/ml, or rhIlL-4 (1000 u/ml) and rhGM-CSF (20 ng/ml), a cytokine combination which leads monocytes to differentiate completely to dendritic cells during seven days of culture (Pickl et al, *J. Immunol.* 157:3850, 1996). MOMC were then harvested, irradiated (1000 rads) and cocultured in triplicate at various MOMC: T cell ratios with $10^5$ allogeneic freshly prepared CD4$^+$ T cells in 0.2 ml RPMI with 5% AB plasma in 96 well tissue flat bottom culture plates. No cytokines were added during coculture. After 4 days [$^3$H]thymidine (1 μCi/well) was added and 18 hours later the wells were harvested and counted. As used herein, the term antigen presenting ability refers to the ability of a cell to stimulate T cells to proliferate, secrete interferon, or generate an immune response.

Figure 4:
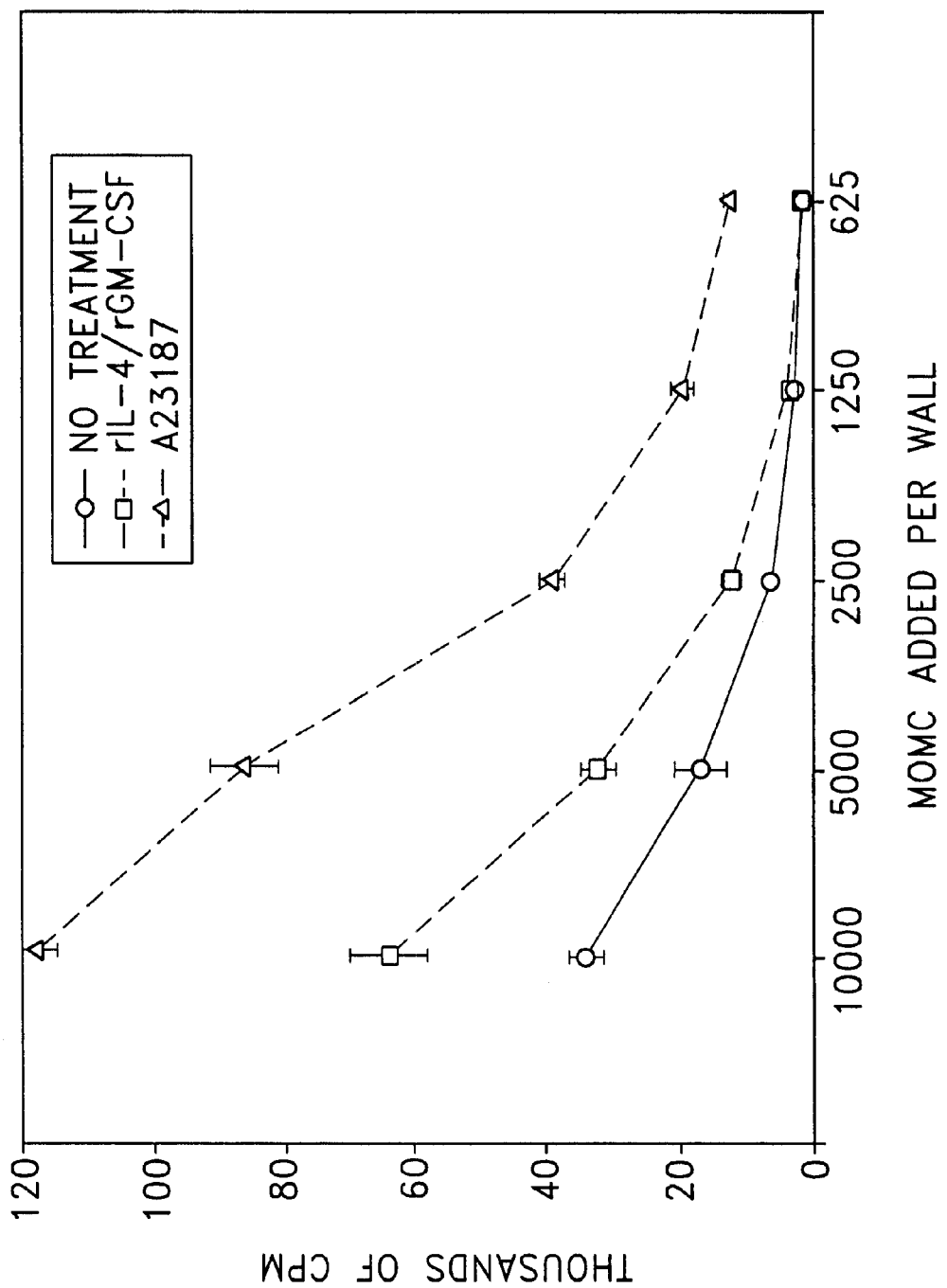
FIG. 4 shows the T cell sensitizing abilities of monocytes treated with calcium ionophore, monocytes treated with rIL-4/rGM-CSF, and untreated monocytes.

The results are shown in FIG. 4. SEM of triplicate wells are displayed as error bars. Results shown are representative of all three donors tested.

On a graded numbers basis ionophore treated monocytes displayed a much greater T cell sensitizing capacity than either rIL-4/rGM-CSF treated or untreated monocytes (ionophore treated >>IL-4/GM-CSF treated>untreated).

Thus, calcium ionophore treatment not only induces upregulation of costimulatory molecules and downregulation of CD14 compared to treatment with cytokine alone, but also hastens acquisition of improved antigen-presenting efficiency.

In addition, calcium ionophore treatment of monocytes dramatically improves their ability to sensitize autologous T cells to specific antigens, as described in Example 8 below.

EXAMPLE 8

Monocyte-rich elutriation fractions from healthy HLA-A2.1 donors were either untreated or treated with ionophore A23187 750 ng/ml for 40 hours, then pulsed with either the M1 influenza-derived peptide or the MART1 melanoma-derived peptide (the M1 peptide is a "recall antigen" for all HLA-A2.1$^{pos}$ individuals, whereas the MART1 peptide is usually a "recall antigen" only for HLA-A2.$^{pos}$ patients with melanoma). Antigen-pulsed monocytes were cocultured with freshly prepared autologous CD8$^+$ T cells for 8–10 days; the T cells were then harvested and cocultured with peptide-pulsed HLA-A2.1 positive T2 stimulator cells which had been pulsed 2 hours with 1 μg/ml of either the MART1 peptide, the influenza M1 derived peptide, or an irrelevant HIV peptide to assess whether specific sensitization to FLU or MART1 peptides was attained.

Figures 5A, 5B:
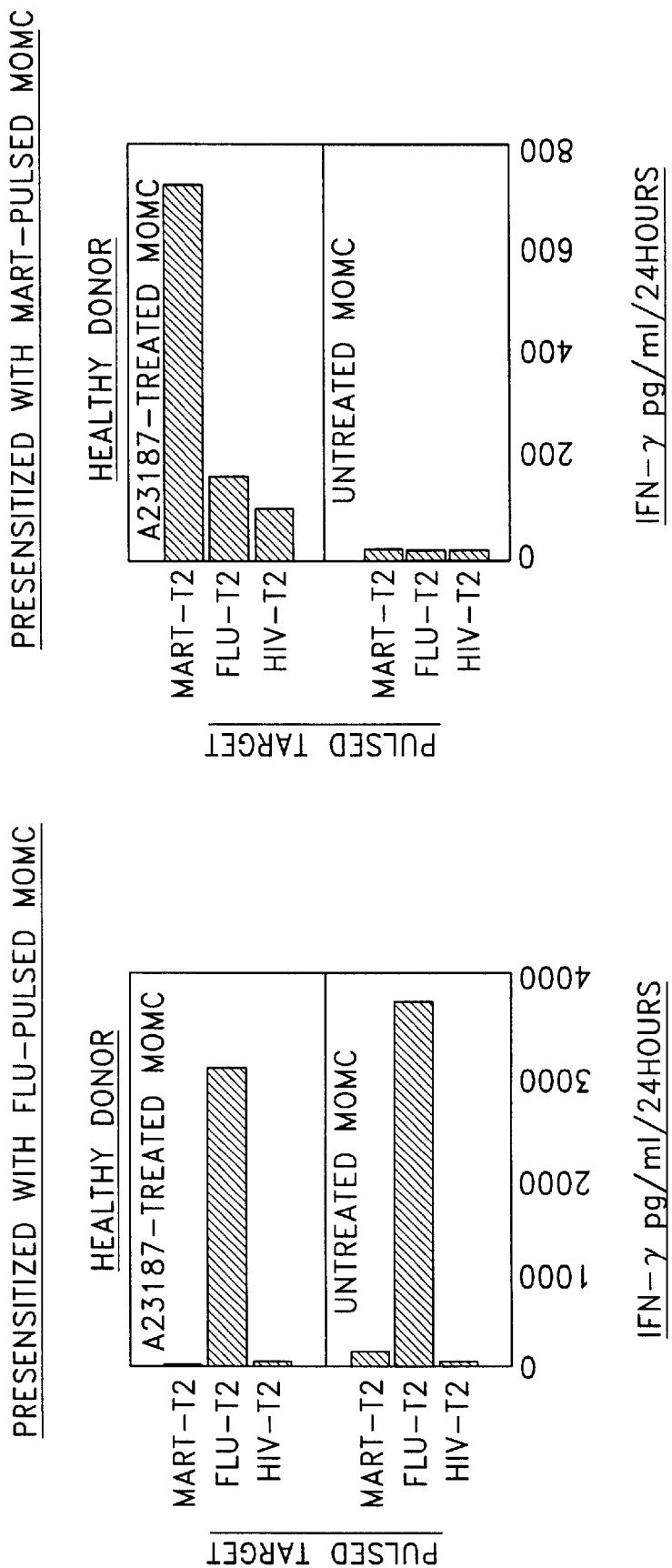
FIG. 5A shows the results of CD8+ T cell sensitization experiments with MOMC pulsed with the influenza peptide.
FIG. 5B shows the results of CD8+ T cell sensitization experiments with MOMC pulsed with the MART-1 peptide.

Secretion of interferon gamma was measured and the results are shown in FIG. 5. FIG. 5A shows the results obtained with MOMC pulsed with the influenza peptide and FIG. 5B shows the results obtained with MOMC pulsed with the MART-1 peptide.

Both untreated and A23187-treated monocytes were equally able to stimulate expansion of the autologous T cell response to the recall antigen M1. In contrast, untreated monocytes could only sensitize autologous T cells to the MART1 peptide for one normal donor out of eight, whereas calcium-ionophore treated monocytes from the same donors could sensitize T cells to MART1 in every instance.

Thus, in circumstances where T cells are not previously sensitized to an antigen (such as is the case for most healthy donors and the MART1 antigen), calcium ionophore-treated monocytes are superior to untreated monocytes for achieving sensitization, consistent with their acquisition of an activated DC phenotype. Other experiments described above also indicate that while contaminant DC in monocyte-rich fractions may contribute to improved T cell sensitization following calcium ionophore treatment, monocytes differentiated to an ADC phenotype by calcium ionophore have equally potent antigen-presenting function as ionophore-treated DC, and possess an equivalent T cell sensitizing capacity even in the absence of contaminant DC.

Maximal responsiveness of monocytes to calcium ionophore observed under the following conditions:

high cell density (3×10$^6$ monocytes per well on standard 24 well plate or higher density)

small monocyte size (smaller monocytes display greater upregulation of B7.1 and downregulation of CD14, for example, than larger monocytes; however, including adjunct cytokines such as rhGM-CSF, IFN-g, IL-2 and/or IL-1 during calcium ionophore treatment markedly augments even large monocyte responses)

select serum batches are more conducive

The optimal doses of ionophore for achieving DC differentiation of monocytes vary among culture media and appear to be related to the protein content (i.e., 375–750 ng/ml is optimal concentration of A23187 in media with 5% AB serum; 180–375 ng/ml for 10% FCS; 45–90 ng/ml for serum free media).

As described in Example 9 below, the ability of calcium ionophores to induce monocytes to express the phenotype of activated myeloid dendritic cells does not depend on the interaction of the monocytes or other myeloid cells with other cell types such as dendritic cells.

EXAMPLE 9

Monocytes in monocyte rich elutriation fractions (90–93% monocytes) were further purified using Miltenyi microsuperparagnetic beads coupled to anti-CD14. After incubation with these beads cells were applied to a magnetized column to positively select the strongly CD14$^{pos}$ cells, and were enriched to >98% purity. Unpurified or purified monocytes were cultured for 40 hours in our standard culture medium with 750 ng/ml ionophore A23187, then harvested. The recovered cells were either immediately FACS analyzed or added in graded numbers to freshly prepared allogeneic T cells to assay their antigen presenting function. Four days later, the T cell cultures were pulsed with $^3$H-TdR (tritiated thymidine) and harvested 18 hours later.

Figure 6A:
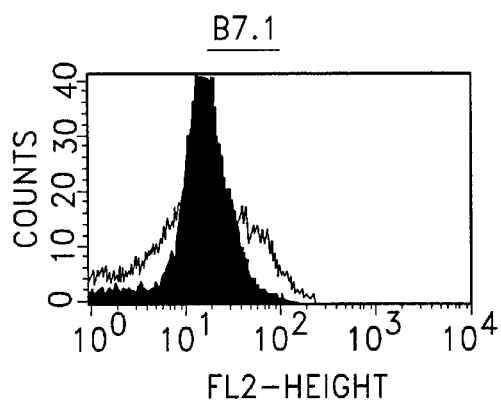
FIGS. 6A–6D show the B7.1 expression patterns of purified $CD14^{pos}$ cells cultured in medium alone, purified $CD14^{neg/dim}$ cells cultured in medium alone, purified $CD14^{pos}$ cells cultured with 750 ng/ml A23187, and purified $CD14^{neg/dim}$ cells cultured with 750 ng/ml A23187.
Figure 6B:
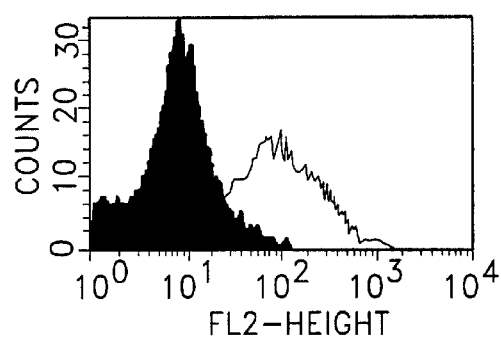
Figure 6C:
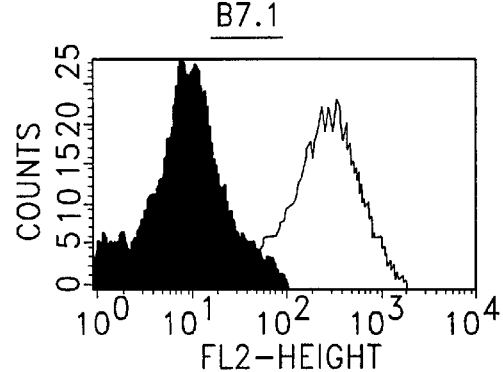
Figure 6D:
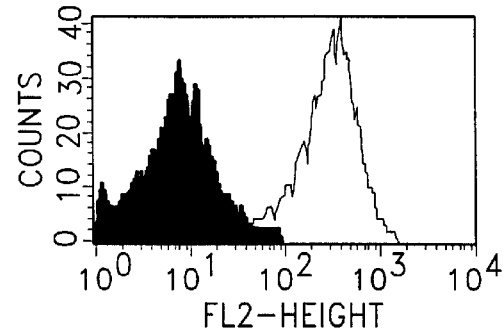
Figure 6E:
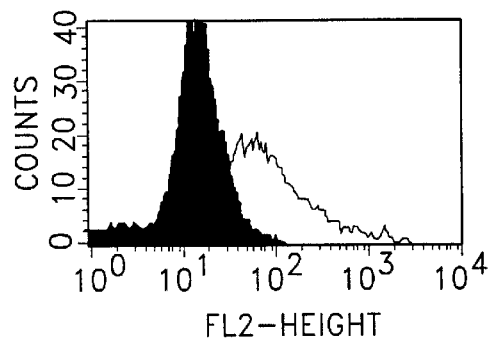
FIGS. 6E–6H show the B7.2 expression patterns of purified $CD14^{pos}$ cells cultured in medium alone, purified $CD14^{neg/dim}$ cells cultured in medium alone, purified $CD14^{pos}$ cells cultured with 750 ng/ml A23187, and purified $CD14^{neg/dim}$ cells cultured with 750 ng/ml A23187.
Figure 6F:
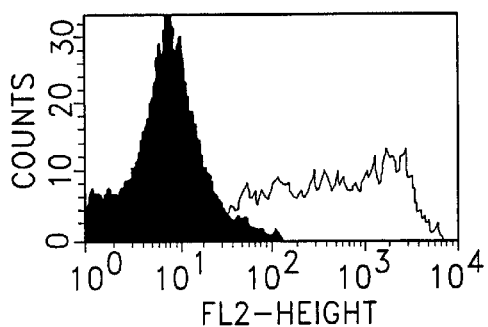
Figure 6G:
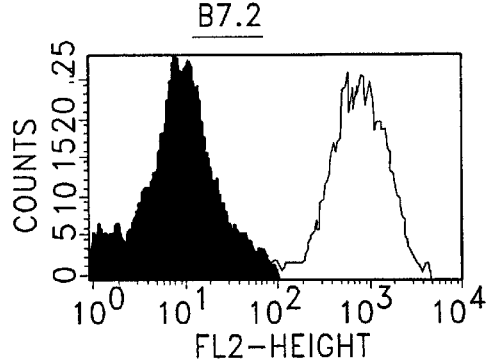
Figure 6H:
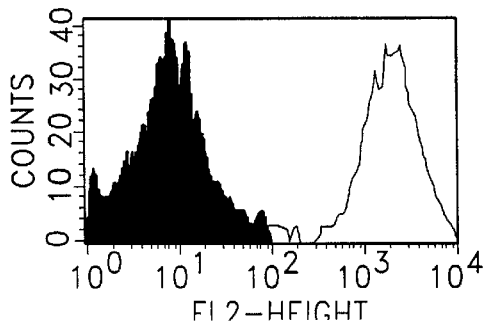
Figure 6I:
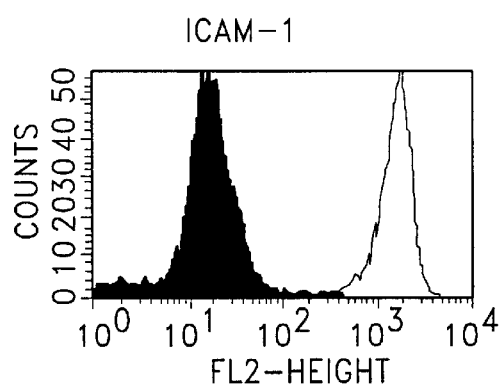
FIGS. 6I–6L show the ICAM-1 expression patterns of purified $CD14^{pos}$ cells cultured in medium alone, purified $CD14^{neg/dim}$ cells cultured in medium alone, purified $CD14^{pos}$ cells cultured with 750 ng/ml A23187, and purified $CD14^{neg/dim}$ cells cultured with 750 ng/ml A23187.
Figure 6J:
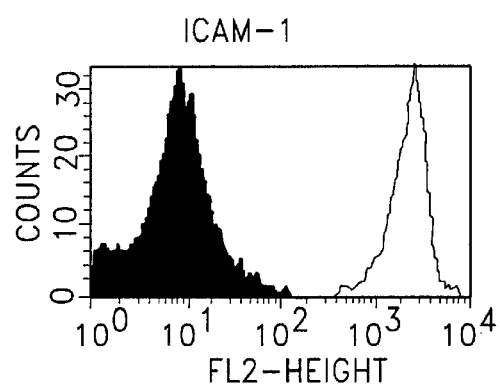
Figure 6K:
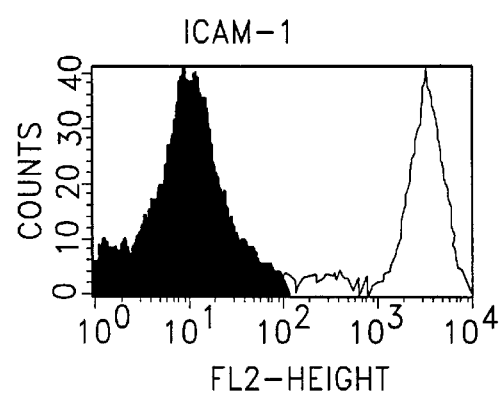
Figure 6L:
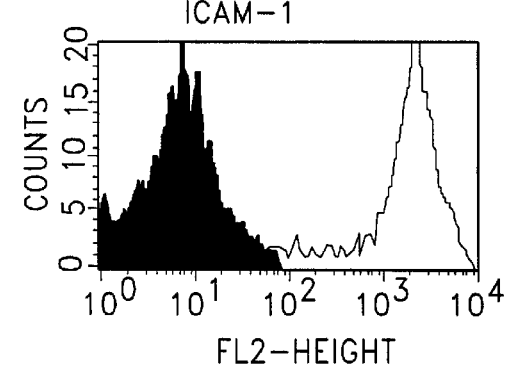
Figure 6M:
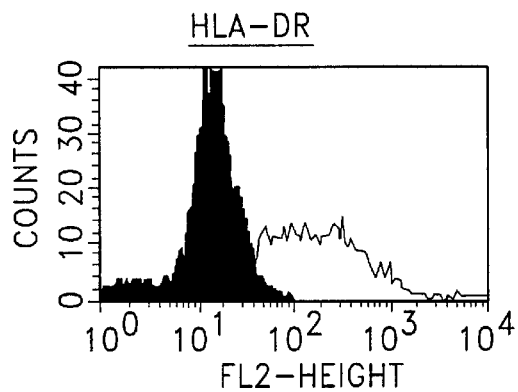
FIGS. 6M–6P show the HLA-DR, HLA-ABC, CD40, and CD83 expression patterns of purified $CD14^{pos}$ cells cultured in medium alone, purified $CD14^{neg/dim}$ cells cultured in medium alone, purified $CD14^{pos}$ cells cultured with 750 ng/ml A23187, and purified $CD14^{neg/dim}$ cells cultured with 750 ng/ml A23187.
Figure 6N:
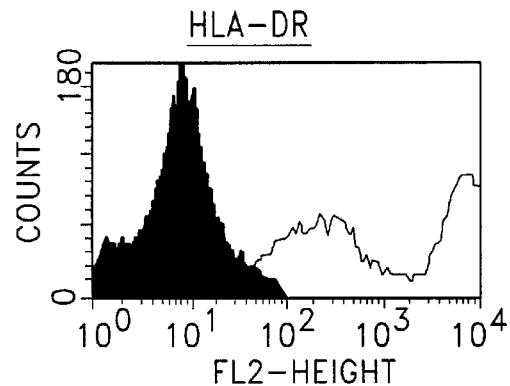
Figure 6O:
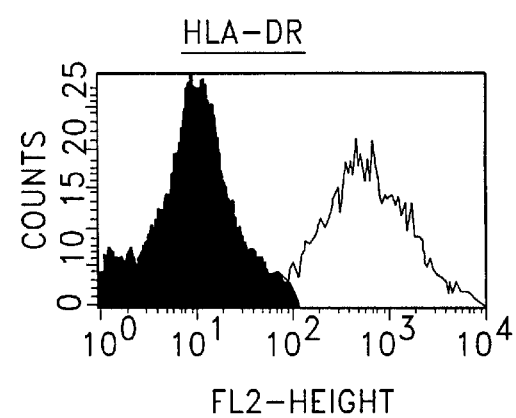
Figure 6P:
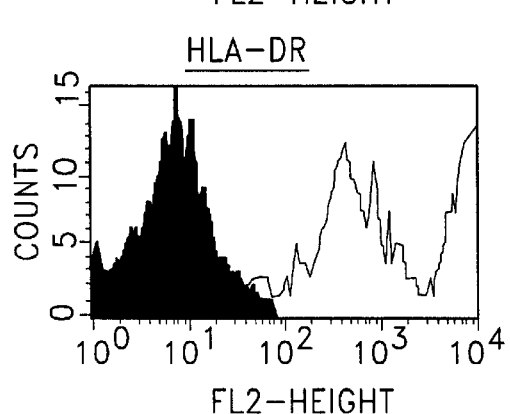
Figure 6Q:
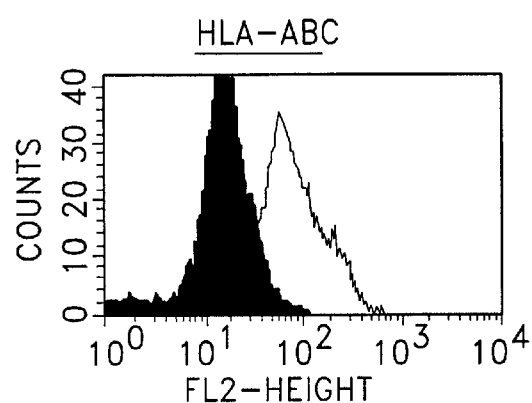
FIGS. 6Q–6T show the HLA-ABC expression patterns of purified $CD14^{pos}$ cells cultured in medium alone, purified $CD14^{neg/dim}$ cells cultured in medium alone, purified $CD14^{pos}$ cells cultured with 750 ng/ml A23187, and purified $CD14^{neg/dim}$ cells cultured with 750 ng/ml A23187.
Figure 6R:
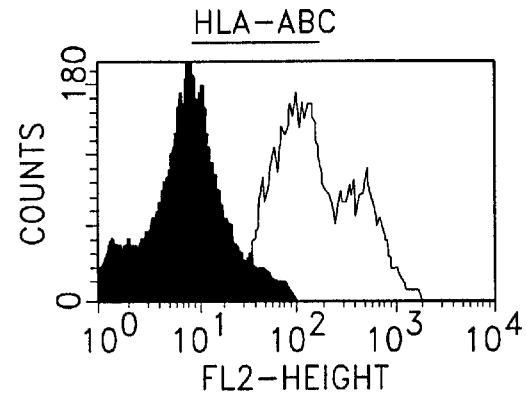
Figure 6S:
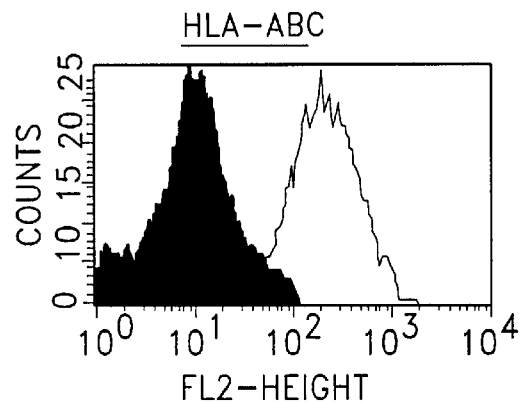
Figure 6T:
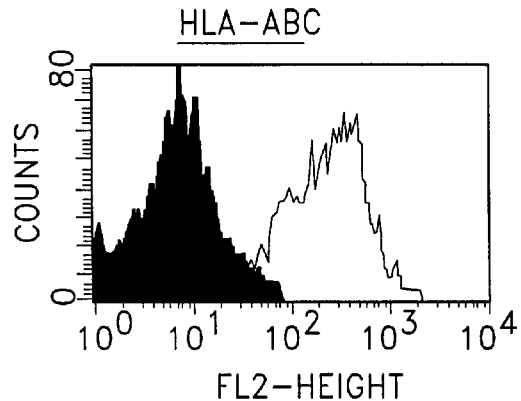
Figure 6U:
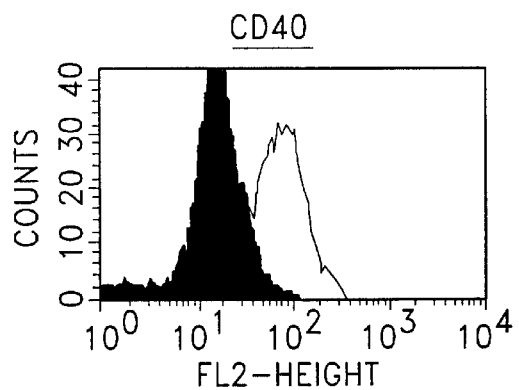
FIGS. 6U–6X show the CD40 expression patterns of purified $CD14^{pos}$ cells cultured in medium alone, purified $CD14^{neg/dim}$ cells cultured in medium alone, purified $CD14^{pos}$ cells cultured with 750 ng/ml A23187, and purified $CD14^{neg/dim}$ cells cultured with 750 ng/ml A23187.
Figure 6V:
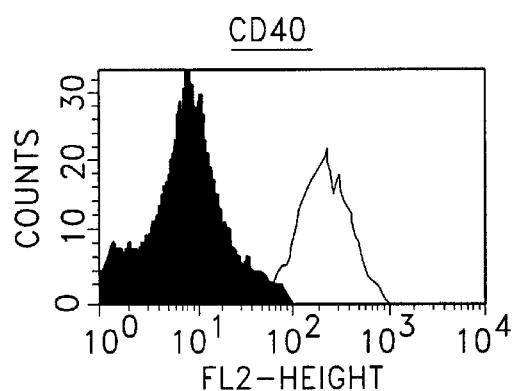
Figure 6W:
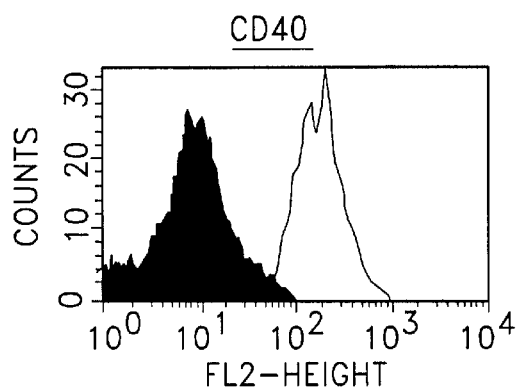
Figure 6X:
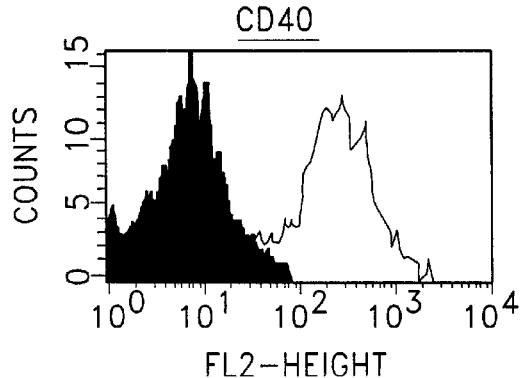
Figure 6Y:
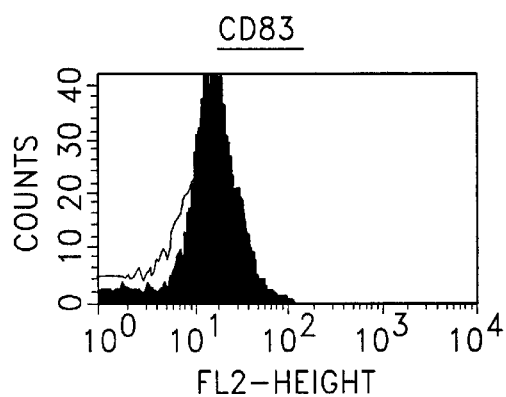
Figure 6Z:
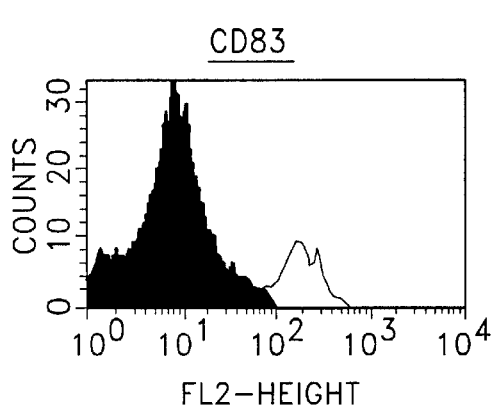
Figure 6A:
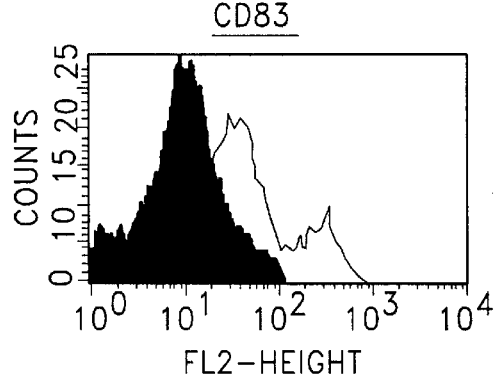
Figure 6A:
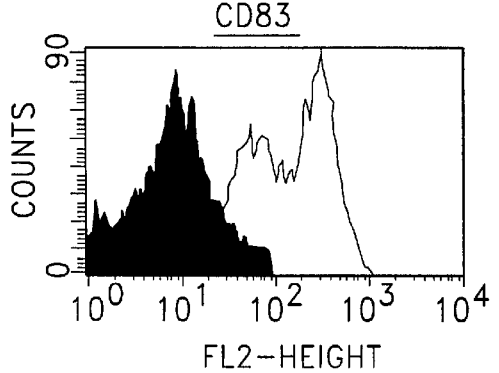

The results of three experiments are shown in FIGS. 6A–6AB. Within each box the filled histogram displays the distribution of control Ab-stained cells, while the unfilled histogram displays the distribution of cells stained with the relevant Ab: [A-D] B7.1 expression; [E-H] B7.2 expression; [I-L] ICAM-1 expression; [M-P] HLA-DR expression; [Q-T] HLA-ABC ABC expression; [U-X] CD40 expression; [Y-AB] CD83 expression. FIGS. 6A, 6E, 6I, 6M, 6Q, 6U, and 6Y: purified CD14$^{pos}$ fraction cultured in medium alone. FIGS. 6B, 6F, 6J, 6O, 6R, 6V, and 6Z: purified CD 14$^{neg/dim}$ fraction cultured in medium alone. FIGS. 6C, 6G, 6K, 6P, 6S, 6W, and 6AA: purified CD14$^{pos}$ fraction cultured with 750 ng/ml A23187. FIGS. 6D, 6H, 6L, 6Q, 6T, 6X, and 6AB: purified CD14$^{neg/dim}$ fraction cultured with 750 ng/ml A23187.

The FACS analysis of FIGS. 6A–6AB demonstrates that purified monocytes downregulated CD14, and upregulated B7.1, B7.2, ICAM-1, HLA-DR, HLA-ABC, CD40 and CD83 equivalently to the monocytes in prepurified fractions. In addition cells calcium ionophore-treated purified monocytes displayed an enhanced T cell sensitizing capacity identical on a cell numbers basis to the ionophore-treated prepurified fraction cells. Thus, the monocyte response to calcium ionophore is not dependent on contaminant cells such as lymphocytes or DC, and the enhanced T cell sensitizing efficiency of ionophore-treated monocytes is also not a reflection of activated contaminant cells.

In addition to monocytes, other cell types may also be induced to express the phenotype of activated myeloid dendritic cells. As will be discussed in greater detail below, the induction of an activated myeloid dendritic cell phenotype in tumor cells is of particular clinical importance. The following section demonstrates that myeloid leukemia cells, such as the HL-60 cell line, may be induced to express the phenotype of activated myeloid dendritic cells. In addition, the following section demonstrates that the above described induction of an activated myeloid dendritic cell phenotype by calcium ionophore treatment results from elevated intracellular calcium levels. Accordingly, the present invention encompasses methods for inducing the phenotype of a myeloid dendritic cell by increasing the intracellular calcium concentration.

III. Elevated Intracellular Calcium Levels Induce the Expression of an Activated Myeloid Dendritic Cell Phenotype Examples 10–16 below demonstrate that the ability of the above agents to induce the expression of an activated dendritic cell phenotype results from an increase in intracellular calcium concentration.

EXAMPLE 10

To demonstrate that an increase in intracellular calcium concentration is responsible for the ability of calcium ionophores or agents which interfere with calcium pumping to induce expression of an activated dendritic cell phenotype, calcium was removed from the culture medium prior to calcium ionophore or thapsigargin treatment.

Calcium was removed from cultured cells by two methods. The first method involved adding EDTA to cells cultured in normal, calcium-containing RPMI. EDTA is a chelator of divalent cations, including calcium and magnesium. EDTA binds tightly to these ions, and while the ions remain in the culture system, the binding of EDTA renders them biologically unavailable to the cells. EDTA had potent toxic effects on human peripheral blood monocytes, and thus monocytes could not be evaluated by this method. However, concentrations of EDTA (<1 uM) that strongly suppressed the effects of ionophore were not toxic to HL-60 cells. In HL-60 cells, CD80 upregulation was suppressed 100% by a 1 uM dose of EDTA, whereas CD86 levels were diminished by more than 85%. Almost identical suppression was seen at a 0.5 uM dose of EDTA, but the suppressive effects rapidly diminished at 0.25 uM.

The second method involved washing the cells extensively in calcium-free RPMI medium, and culturing them in the same calcium-free medium supplemented with serum that had been dialyzed against calcium-free phosphate-buffered saline. Thus no calcium was present in the cultures. Use of calcium-free RPMI and dialyzed serum had similar effects on HL-60 cells. The ionophore-induced upregulation of both CD80 and CD86 were almost 100% ablated under calcium-free conditions.

The effect of calcium-free RPMI and dialyzed serum on ionophore-treated monocytes was also tested. Upregulation of monocyte B7.1 expression was suppressed 100% and CD14 downregulation was suppressed 53% when calcium was omitted from the medium.

Thus, calcium ionophore induces monocytes and other myeloid-origin cells to acquire the phenotype of activated myeloid dendritic cells by increasing the intracellular calcium level The role of calcium in inducing the expression of an activated myeloid dendritic cell phenotype is consistent with its role in regulating other cellular activities, such the modulation of gene expression. For example, engagement of the T cell receptor (TCR) on T lymphocytes is one of at least 2 signals that T cells must be provided in order to initiate transcription of the interleukin-2 (IL-2) gene. Engagement of the TCR initiates a number of biochemical events necessary for IL-2 gene transcription, one of these being an elevation in levels of cytoplasmic calcium. An enzymatic cascade then transduces the calcium signal to activate transcription of the iL-2 gen as follows.

Calcium is capable of binding to and activating a cytoplasmically localized regulatory protein called calmodulin. Calmodulin has no known enzymatic function itself, but it can in turn bind to and activate a number of enzymes, including the serine/threonine protein phosphatase, calcineurin, and a series of calmodulin-dependent protein kinases. These enzymes can then act on and alter the activation status of a number of nuclear transcription factors which bind to discreet promoter regions and control the transcriptional activity of specific genes. In T lymphocytes, calcineurin acts on the nuclear factor of activated T cells (NF-AT), activating it through dephosphorylation. The activated NF-AT then translocates to the nucleus and binds to specific regions of the IL-2 gene where, in cooperation with other nuclear factors (activated through other pathways), it directs IL-2 transcription.

A number of pharmacologic agents have been developed that can interrupt this particular calcium activation pathway at discrete points. For example, calmodulin activity can be suppressed by the drugs trifluoperazine dimaleate and W-7. Some of the calmodulin-dependent kinases can be blocked by compounds such as KN-62 and KT-5926. One highly specific inhibitor of calcineurin activity is the immunosuppressive drug, Cyclosporine A. Examples 11–14 below demonstrate that agents which interfere with the activities of enzymes involved in the transduction of the calcium response block the ability of calcium ionophore to induce the expression of an activated myeloid dendritic cell phenotype.

As described in Example 11 below, calmodulin antagonists attenuate ionophore-induced acquisition of ADC features in both monocytes and cells having a myeloid origin, such as HL-60 cells.

EXAMPLE 11

HL-60 cells treated with 188ng/ml A23 187 for 24 hours in the presence of calmodulin antagonists trifluoperazine dimaleate (TpD) (25-1 uM) or W-7 (50-1 uM) exhibited significantly attenuated levels CD80 expression relative to cells which received A23187 alone. The optimal concentration of TpD (10 uM) inhibited ionophore-induced up-regulation of CD80 by over 90%, while the optimal concentration of W-7 (50 uM) inhibited CD80 expression by over 75%.

Similarly, the optimal concentration of TpD (10 uM) inhibited CD80 and CD86 in peripheral blood monocytes by over 50%. This drug also had significant suppressive effects on CD40, HLA-DR and HLA-ABC for peripheral blood monocytes.

As described in Example 12 below, calmodulin kinase inhibitiors also blocked the calcium ionophore mediated induction of an activated dendritic cell phenotype.

EXAMPLE 12

The calmodulin kinase inhibitors KN-62 (20 uM) or KT-5926 (1 uM) was added to HL-60 cells in the presence of 188 ng/ml A23187. Twenty four hours later the level of CD80 was analyzed. KN-62 led to inhibition of CD80 expression at levels of greater than 50% for each inhibitor.

Similar effects were seen on peripheral blood monocytes. Monocytes treated with 750 ng/ml ionophore and KT5926 (1 uM) were found 24 hours later to be suppressed for CD80 (>60%), CD86 (about 50%), and CD40 (>50%). HLA-ABC was also suppressed over 40%, with modest, but detectable suppression also of HLA-DR.

As described in Example 13 below, the calcineurin antagonist and immunosuppressive drug cyclosporine A attenuates calcium ionophore-induced acquisition of an activated myeloid dendritic cell phenotype.

EXAMPLE 13

Cyclosporine A (CsA) (5-.00005 ug/ml) was added to HL-60 cells along with 188 ng/ml A23187, harvested 24 hours later, and subjected to FACS analysis. The optimal concentration of CsA (0.5 ug/ml) led to over a 90% inhibition of ionophore-induced CD80 expression, and an 80% inhibition in CD86, and ICAM 1 expression. Human peripheral blood monocytes treated with 750 ng/ml A23187 plus CsA also showed suppression of ionophore-induced expression of CD80 (>70%) CD86 (>85%) and CD40 (>45%). However, levels of ionophore-induced enhancement of HLA-ABC and downregulation of CD14 were unaffected, while HLA-DR expression was further enhanced by addition of CsA (15–20%).

Treatment of HL-60 cells with CsA markedly antagonized the improved antigen presenting function normally induced by calcium ionophore treatment. HL-60 cells were treated with or without 0.5 uG/ml CsA, then treated with 188 ng/ml calcium ionophore A23817, with or without rhIFN-gamma 1000 u/ml and rhGM-CSF 20 ng/ml for 72 hours. Fresh allogeneic naive (CD45R0 negative) T cells were prepared and cocultured with graded numbers of irradiated (3000R) HL-60 cells treated under the above-described conditions. Four days later the cultures were pulsed with $^3$H-TdR (tritiated thymidine) and harvested 18 hours later. It was found that including CsA in the HL-60 cultures markedly inhibited their antigen-presenting function, as displayed by their essentially complete loss of T cell allosensitizing capacity.

Agents which increase the intracellular calcium concentration by blocking calcium export out of the cytoplasm also induce the expression of an activated myeloid dendritic cell phenotype. Most cell types normally pump cytoplasmic calcium ions from the cytoplasm of the cell to the exterior of the cell (across the plasma membrane) as well as into membrane bound intracellular storage sites through an energy-dependent process. Thus, normal resting cells have low cytoplasmic concentrations of $[Ca^{++}]$ relative to the cell exterior, as well as to interior sequestration sites. The primary known pharmacologic effect of calcium ionophores is the permeabilization of cell membranes to calcium ions, which leads to "leakiness" of the cell membrane, and the inability of the cell to keep cytoplasmic calcium concentrations low. As described in Example 14 below, the drug thapsigargin, which inteferes with the calcium pumping mechanism of cells, is able to induce both monocytes and the myeloid leukemia cell line HL60 to express the phenotype of activated myeloid dendritic cells.

EXAMPLE 14

Thapsigargin was added to cultures of human peripheral blood monocytes (prepared as describe in more detail below) or the human myeloid-origin leukemia line, HL-60, which has a response to calcium ionophore treatment very similar to that of monocytes. Thapsigargin was added to cultured human peripheral blood monocytes and HL-60 cells in concentrations ranging from 0 to 1000 nM. Cells were harvested 24 hours later and evaluated for the acquisition of ADC immunophenotypic characteristics by FACS analysis.

Generally, thapsigargin had dose-dependent effects on both monocytes and HL-60 which were strikingly similar to those of ionophore, albeit of a somewhat lower magnitude. Upregulation of CD80, CD86, CD40, HLA-DR, HLA-ABC, ICAM-1, and CD83 were observed in human monocytes at a 750 nM dose of thapsigargin that were about 50% the magnitude observed with an optimal (750 ng/ml) dose of A23187. Thapsigargin also downregulated monocyte CD14 expression about 75% as effectively as ionophore.

HL-60 cells posted an optimal response to thapsigargin at a 250 nM dose, and likewise showed enhanced expression of CD80, CD86, and ICAM-1. Levels achieved were 50–75% of those observed with ionophore. HL-60 cells do not constiutively express CD 14.

Thus, both calcium ionophore treatment and treatment with agents which increase intracellular calcium levels by interfering with the calcium pumping mechanisms of cells induce both monocytes and myeloid leukemia cells to express the phenotype of activated myeloid dendritic cells.

Not every agent which increases intracellular calcium levels is capable of inducing monocytes to express the phenotype of activated myeloid dendritic cells. For example, a variety of chemokines which have been demonstrated by others to induce monocyte chemotaxis (a process which involves localized subcellular $[Ca^{++}]$ fluxes which induce the monocyte to move in that particular direction), such as MIP-1-alpha, MCP-1 and RANTES, as well as chemotactic peptides such as f-MET-LEU-PHE, do not induce monocytes to express the phenotype of activated myeloid dendritic cells, as described in Example 15 below. Thus, the methods of the present invention involve contacting monocytes with an agent having the ability to raise the intracellular calcium concentration to a level effective to induce the expression of an activated myeloid dendritic cell phenotype.

EXAMPLE 15

Freshly thawed monocytes for 20–40 hours were incubated with a wide dose range of the chemokines listed above (e.g., 1–100 ng/ml MIP-1-alpha), either alone or in combination, then harvested the cells and assayed for acquisition of typical activated dendritic cell characteristics such as CD80 and CD83 expression. Even at high doses these agents had a negligible ability to induce these DC characteristics.

As described in Example 16 below, the ability of agents to cause acquisition of dendritic cell characteristics correlates to the magnitude of $[Ca^{++}]$ flux they generate in monocytes.

EXAMPLE 16

Calcium-chelation luminescence spectrophotometry was utilized to measure intracellular calcium fluxes in monocytes. Monoytes were incubated with 5 uM/ml indol, a calcium chelating agent which emits fluorescence at different wavelengths (405 or 480 nm) depending on whether or not it is bound to cycloplasmic calcium. Increased calcium mobilization causes relative shifts in emission from one wavelength to the other. After 30 minute incubation with indol, monocytes were washed, pulsed with a variety of agents such as calcium ionophore, virus, f-MET-LEU-PHE, or LPS. To measure calcium fluxes at subsequent time intervals, cells were stimulated with a 355 nM wavelength beam, and fluorescence emission measured at 405 and 480 nm.

It was found that calcium ionophore treatment in the 180–750 ng/ml range resulted in marked sustained monocyte mobilization. While, as expected, all other studied agents caused lower and less sustained calcium flux compared to calcium ionophore treatment, treatment with adenovirus was by far the most potent of the non-ionophore agents. The chemotactic peptide f-MET-LEU-PHE, which does not induce monocytes to achieve DC differentiation, produced only a brief calcium flux of much lower magnitude compared to adenovirus or calcium ionophore treatment.

In other experiments (see below) we have demonstrated that adenovirus induces the phenotype of an activated myeloid dendritic cell overnight, whereas the chemotactic peptide f-MET-LEU-PHE does not induce that phenotype.

Thus, pronounced cytoplasmic calcium fluxes are demonstrable in monocytes when they are treated with agents which result in overnight acquisition of the signature immunophenotypic changes associated with calcium mobilization treatment.

In addition to the agents specifically described above which produce intracellular calcium levels effective to induce monocytes or other myeloid cells to express the phenotype of activated myeloid dendritic cells, it is likely that other treatments will also produce intracellular calcium levels effective to induce monocytes or other myeloid cells to express that phenotype. For example, CD40 ligand in combination with IFN-gamma or GM-CSF treatment is likely to induce monocytes or myeloid cells to express the phenotype of activated myeloid dendritic cells.

CD40 ligand (CD40L) is markedly upregulated on T cells following minimal activating signals such as T cell receptor (TCR) engagement (REF: Nishioka, U. and P. E. Lipsky. 1994. The role of CD40-CD40 ligand interaction in human T cell-B- cell collaboration. *J. Immunol.* 153: 1027). Crosslinking of CD40L on T cells with the reciprocal molecule, CD40, on B cells, results in marked calcium mobilization in B cells leading to proliferation; this effect on B cells can be blocked with FK506, a drug which like Cyclosporine A (CsA) also blocks the enzyme calcineurin (Gerry, G, B. Klaus, M. S. K. Choi and M. Holman. 1994. Properties of mouse CD40: Ligation of CD40 activates B cells via a $Ca^{++}$-dependent, FK506-sensitive pathway. *Eur. J Immunol.* 24:3229). Other investigators have demonstrated that peripheral blood dendritic cells can further be activated through CD40L stimulation and CD34 positive progenitor cells can also be made to differentiate with CD40L stimulation. However, no one has demonstrated differentiation effects on monocytes or linked stimulation of dendritic cells or CD34 positive progenitor cells by CD40L to increased intracellular calcium levels. Flores-Romo, L. et al. *J. Ex. Med.* 1997 185:341–349; Caux, C. et al. *J. Ex. Med.* 1994 180:1263–1272.

Since monocytes express CD40, which can easily be upregulated further by cytokines such as IFN-gamma or AGM-CSF, and since many of the effects of calcium ionophores on monocytes, such as B71/B72 upregulation, are mediated through calcineurin (i.e., are CsA blockable) it is likely that the engagement of CD40L on T lymphocytes or other cells with CD40 on monocytes will generate calcium mobilization, which may be of sufficient magnitude to cause DC differentiation. The influence of CD40L-CD40 interaction on monocyte phenotype may be evaluated as described below in Example 17.

EXAMPLE 17

Coincubating monocytes for 40 hours with T cells in wells coated with anti-CD3 (which putatively stimulates rapid upregulation of CD40L on T cells) results in downregulation of monocyte CD14 and de novo expression of CD83 and CD80, consonant with the hypothesis that CD40L stimulation of monocytes may confer a calcium mobilization signal sufficient to cause differentiation to an activated DC (ADC) phenotype. It remains possible, however, that other surface molecules or secreted cytokines, instead of or in addition CD40L, are responsible for the differentiation effect.

To demonstrate that CD40L/CD40 interaction induces the expression of an activated myeloid dendritic cell phenotype, the following experiments may be performed. Monocytes are coincubated with immobilized CD40L to see whether this specific molecule is capable of inducing monocytes to express an activated myeloid dendritic cell phenotype, and whether adjunct cytokines such as IFN-gamma and/or GM-CSF (which upregulate CD40 on monocytes) enhance such an effect.

To confirm that induction by CD40L/CD40 interaction is calcineurin dependent the ability of CsA or FK506 to block induction is evaluated as described above. In addition, calcium flux assays are performed as described above to confirm significant calcium flux upon CD40L/CD40 interaction.

IV. Preparation of Monocytes By Venipuncture/Ficoll Separation/Adeherence or Leukapheresis/Ficoll Separation/Adherence Monocytes prepared by methods other than countercurrent centrifugal elutriation can also be induced to express the phenotype of activated myeloid dendritic cells. For example, the simple method described in Example 18 below may also be used to prepare monocytes which are to be induced to express the phenotype of activated dendritic cells. In the method of Example 18, peripheral blood cells comprising monocytes and other mononuclear cells are obtained. If desired, the monocytes in the preparation of peripheral blood mononuclear may be enriched using techniques such as adherence.

EXAMPLE 18

Blood was drawn in heparinized syringes (approximately 80 cc), diluted 1:1 with normal saline, layered on Ficoll-Hypaque, and centrifuged for 20 minutes to remove neutrophils and red blood cells. The peripheral blood mononuclear cell (PBMC) containing interface were washed, counted, and added to 24 well plates, 2 cc culture medium per well, $2 \times 10^7$ cells per well.

After 60 minutes the non adherent cells were removed, leaving a half confluent surface of adherent cells in each well (i.e., monocyte enrichment by adherence) Wells were either untreated or treated with calcium ionophore A23 187 750 ng/ml, and harvested 20 hours later.

Recovered cells in the untreated group contained variable mixtures of monocytes and contaminant lymphocytes which could be distinguished on FACS analysis by their different size and granule content (forward and side scatter analysis). The monocyte subpopulation as $CD14^{pos}$, and had a profile of B7.1, B7.2, HLA-DR, HLA-ABC, and CD83 expression to similar to that observed for untreated elutriated monoytes.

In contrast, the A23187-treated group demonstrated uniform CD14 downregulation, as well as upregulated B72, HLA-DR, and CD40 expression, and de novo B7.1 and CD83 expression.

These studies indicate that monocytes enriched by relatively inexact procedures (Ficoll, adherence selection) respond to calcium ionophore treatment similarly to monocytes enriched by more exacting procedures (leukapheresis/elutriation, or leukapheresis/elutriation/Miltenyi bead enrichment.

Similar results were also obtained starting with leukapheresis cells, prepared as described above, which were then separated on Ficoll-Hypaque and adhered to enrich for monocytes, rather than subjected to countercurrent centrifugal elutriation.

As described in Example 19 below, the monocyte subpopulation present in mixed peripheral blood mononuclear cell (PBMC) fractions also respond to calcium ionophore (CI) treatment in a manner analogous to elutriated monocytes.

EXAMPLE 19

PBMC were prepared by leukapheresis and Ficoll-Hypaque and placed in culture. Since the cells were never elutriated and no adherence step was performed, these cultures deliberately included large numbers of T, B, and NK lymphocytes as well as monocytes. The medium was our standard RPMI 10% human AB serum with antibiotics including amphotericin B. Cells were either untreated or treated for 40 hours with calcium ionophore A23187 750 ng/ml. Cells were then harvested and analyzed by FACS. Cells were stained with FITC conjugated anti-CD3, anti-CD40, anti-CD57, anti-CD 14, or the combination; in addition cells were stained with PE conjugated control antibodies, anti-B7.1, anti-B7.2, etc. In this way the effect of calcium ionophore treatment on each parameter could be clearly delineated.

The monocyte subpopulation within the PBMC was 13–15% of the total recoverable cells. The response of this subpopulation to ionophore treatment was identical to the response of calcium ionophore-treated purified monocytes: e.g., downregulation of CD14 to a background level, seven fold increased B7.1 expression, 10 fold increased B7.2 expression, 4.5 fold increased ICAM-1 expression, 9 fold increased HLA-DR expression, 7 fold increased CD40 expression, and 11 fold increased CD83 expression.

Thus, the monocyte subpopulation within the calcium ionophore-treated group of PBMC responded similarly to calcium ionophore treated elutriated monocytes. Therefore, unenriched monocytes within PBMC fractions (obtainable from leukapheresis or heparinized syringes) can acquire an activated DC immunophenotype following calcium ionophore treatment, and may serve even in this less enriched state as a useful source of antigen-presenting cells. The upregulated expression of costimulatory and MHC molecules on lymphocytes also present during treatment may further contribute to the antigen-presenting potency of calcium ionophore treated PBMC.

V. Induction of an Activated Myeloid Dendritic Cell Phenotype with Adenovirus

In addition to calcium ionophore treatment and treatment with pharmacological agents which increase the intracellular calcium concentration, biological agents may also induce monocytes or other myeloid cells to express the phenotype of activated myeloid dendritic cells. For example, as described in Example 20 below, adenovirus infection induces monocytes to express the phenotype of activated myeloid dendritic cells.

EXAMPLE 20

In numerous experiments, monocytes were cultured 20–40 hours with a wide MOI concentration dose range of adenovirus (strain Ad TK5), then assayed for acquisition of activated DC (ADC) characteristics.

Such adenovirus treatment induced typical ADC characteristics overnight, including de novo CD83 and CD80 expression, upregulated B7.2, CD40, ICAM-2 and HLA-DR expression, downregulated CD14 expression. This effect could be demonstrated for several different adenovirus preparations, including E1 and E3 replication deficient mutants. In the case of Lac Z transfected adenovirus, sublethal concentrations of virus (250 MOI or greater) which resulted in near-uniform infectivity of monocytes (demonstrated by beta-galactosidase expression from the Lac Z gene) were also most effective for causing induction of activated DC (ADC) characteristics.

VI. Positive and Negative Modulation of the Effects of Agents which Increase the Intracellular Level A number of other agents can modulate the ability of agents which increase the intracellular calcium concentration to induce the expression of an activated dendritic cell phenotype. As described above, monocytes treated with calcium ionophore alone have superior antigen-presenting efficiency compared to untreated monocytes and can consistently induce rapid primary autologous T cell sensitization to a variety of antigens, including the HLA-A2.1 restricted melanoma-associated peptide MART1. However, despite this improved efficiency monocytes treated with ionophore alone cannot always induce rapid sensitization to other peptides, such as the HLA-A2.1 ovarian-cancer associated HER2neu (369–377) peptide. It is therefore useful to enhance ionophore's effects to improve efficiency of T cell sensitization.

Conversely, it may be possible using agents which produce negative or mixed modulations in conjunction with ionophore treatment to induce special effects on T lymphocytes, such as tolerance or apoptosis, rather than sensitization.

For this reason, the effects of various agents on induction of the activated myeloid dendritic cell phenotype were studied. These agents fell into four categories.

The first category was agents which had no or little effect alone but which enhanced the induction of an activated myeloid dendritic cell phenotype when added to calcium ionophore treatment. Examples of these agents include endotoxin (0.1–1 ng/ml dose range) and amphotericin B.

The second category was agents which had multiple modulating effects when the agent was added to monocytes without ionophore, but which enhanced CD14 downregulation and upregulation of costimulatory, MHC, and other molecule expression when added in combination with calcium ionophore. These agents do not typically result in selective enhancement of single dendritic cell markers, but rather enhance a wide spectrum of ionophore effects. Examples of agents in this category are rhGM-CSF, rhIL-4, rhIL-12, rhIL-2, rhTNFalpha; rhIFN-gamma, okadaic acid (inhibitor of protein phosphatases I and IIA), staurosporine (inhibitor of serine-threonine kinase), dibutryl cGMP (cGMP analog), and 2'5'-DDA (adenylate cyclase antagonist).

The third category was agents which had variable effects when added without ionophore and which, when added with ionophore, inhibited at least some of the ionophore's effects resulting in overall negative or mixed modulations. Examples of agents in this group are biologic "immunosuppressive" agents such as rhIL-10, glucocorticoids (prednisolone), prostaglandins (PGE2), TGF-beta, pharmacologic agents including cyclosporine A (calcineurin antagonist), KT5926 and KN62 (calmodulin-dependent kinase inhibitors), trifluoperazine and W-7(calmodulin inhibitor), herbimycin A (tyrosine kinase inhibitor), forskolin (adenylase cyclase activator), dibutryl cAMP (adenylate cyclase analog), KT5823 (protein kinase G antagonist), and KT720 (protein kinase A antagonist).

The fourth group comprises agents which have to date had little or no effect on ionophore-induced monocyte differentiation. These agents include chelerythrine chloride (protein kinase C antagonist) rhIL-1 alpha, rhIL-6.

As described in greater detail below, many agents such as endotoxin (LPS), rhGM-CSF, rhIL-2, rhIL-12, rhIFN-g, rhTNF-a, rhIL-4, the antibiotic amphotericin B, and others enhance the immunophenotypic activating effects of calcium ionophore treatment. In order to define the "pure" (i.e., unenhanced) effects of calcium ionophore, the ionophore's effects when added in the absence of any of the above agents were compared to the effects of several cytokines added without ionophore. For this assay, particular cytokine combinations (rhIL4, rhGMSF, and rhTNF-alpha ) were selected which have been shown by other investigators to induce monocytes to differentiate into dendritic cells over a seven day period (as opposed to the more rapid differentiation described above which is achieved with calcium ionophore) (Pickl et al,. *J. Immunol.* 157:3850, 1996; Zhou and Tedder, *Proc. Natl. Acad. Sci. U. S. A.* 93:2588, 1996). In these experiments, the antibiotic amphotericin B, which is normally a component of our culture medium, was omitted and the endogenous endotoxin content of the culture medium was estimated to be below stimulatory range (under 0.1 ng/ml).

EXAMPLE 21

Monocyte predominant elutriation fractions were thawed and cultured in our standard culture medium with 10% AB human serum, (with amphotericin B omitted, low endotoxin conditions), under each of the following conditions: (a) no additive; (b) A23187 750 ng/ml; (c) rhIL4 1000 u/ml; (d) rhIL4 1000 u/ml+rhGM-CSF 100 ng/ml; (e) rhIL4 1000 u/ml, rhGM-CSF 100 ng/ml and rhTNF-alpha 100 u/ml. A separate well for each of the above conditions was also prepared, but preincubated for one hour in Cyclosporine A (CsA) 0.5 uG/ml. After 20 hours culture the cells were harvested and FACS analyzed; immunophenotypic effects were gauged by comparing cell surface molecule expression at 20 hours to original expression prior to culture.

The effects of A23187 treatment at 20 hours were similar to but of a slightly lower magnitude than than typically seen when 0.5–2 ug amphotericin B or 0.1–1 mg/ml endotoxin is also added to the medium. CD14 expression was downregulated 90% following 20 hours of A23187 treatment, but downregulated only 0–20% with any of the above cytokine treatments. B7.1 expression increased 14 fold following A23187 treatment, but only 3.4–7.3 fold following the cytokine treatments. B7.2 expression increased 7.5 fold following A23187 treatment, but only 1.7–3.7 fold following the cytokine treatments. HLA-DR increased 2.9 fold following A23187 treatment, but only 1.1–2.1 fold following the cytokine treatments. HLA-ABC expression increased 3.0 fold following A23187 treatment, but did not markedly change (0.8–1.3 fold difference) following the cytokine treatments. CD83 expression increased 8.7 fold and was uniform following A23187 treatment, but increased less (3.2–5.5 fold) and was only heterogeneously expressed following the cytokine treatments. HLA-DQ expression increased 3.4 fold following A23187 treatment, and also to a similar degree (2.3–5.2 fold) following the cytokine treatments.

0.5 ug/ml Cyclosporine A (CsA) had marked inhibitory effects (50% or greater) on several effects induced by calcium ionophore treatment; B7.2 upregulation was inhibited 79% and B7.1 upregulation was inhibited 56%. In contrast, the B7.1 and B7.2 upregulation observed following the cytokine treatments (without ionophore) was either enhanced or only modestly suppressed (always <40%) by CsA.

Thus, even in the absence of enhancing agents, the effect of calcium mobilization on monocytes is distinguishable after overnight culture from the effects of those cytokine treatments which lead to slower differentiation. The composite profile of rapid calcium mobilization effects (CD14 downregulation, marked B7.1 and B7.2 upregulation and uniform de novo CD83 expression at 20 hours, as well as marked blockade of B7.2 and B7.1 expression by CsA) is distinctive from the effects of studied cytokine/cytokine combinations after a similarly short culture inverval.

Example 22 below describes the functional enhancement of T cells using modulatory factors.

EXAMPLE 22

Monocytes were cultured for 40 hours either without treatment, calcium ionophore A23187 (750 ng/ml) or A23187 plus a cytokine cocktail of rhIL-2 (300 IU/ml), rhIL-12 (20 ng/ml) and rhGMCSF (20 ng/ml). After 40 hours, the cells were pulsed with a tumor derived HER2neu (369–377) peptide for two hours, harvested, then FACS analyzed or cocultured for 8–10 days with naive autologous $CD8^+$ T cells to determine whether rapid sensitization to the HER2neu peptide could be achieved.

FACS analysis showed that when rhGM-CSF, rhIL-2 and rhIL-12 were added to calcium ionophore treatment marked enhancement of B7.1, B7.2, HLA-DR and HLA-DQ expression occurred, as well as enhanced CD 14 downregulation compared to ionophore treatment alone.

Similar effects were seen with the combination of calcium ionophore and rhIFN-gamma or ionophore and rhIFN-gamma plus rGM-CSF.

In the majority of patients for whom this protocol was run, T cell sensitization to HER2neu peptide could not be achieved with either untreated monocytes or monocytes treated with calcium ionophore alone, as evidenced by a lack of specific IFN-gamma secretion when harvested T cells were cultured with appropriate HER2neu-pulsed stimulator cells. In contrast, monocytes treated with the combination of ionophore, rGM-CSF, rIL-2, and rIL-12 were more consistently effective for inducing T cell sensitization to the peptide.

Thus, agents which enhance calcium ionophore's upregulation of costimulatory, MHC and other molecules on monocytes can further improve antigen-presenting function. Cells having such further improved antigen presenting ability may be preferred for treating certain conditions via T cell sensitization.

Other agents may be used to inhibit T cell stimulation as described in Example 23 below.

EXAMPLE 23

HL-60 leukemia cells, which respond to calcium ionophore in a manner analogous to monocytes as described above, were variously treated as follows: no treatment, rhGM-CSF (20 ng/ml) and IFN-gamma (1000 u/ml); A23187 (180 ng/ml) alone; A23187, rhGM-CSF and IFN-gamma combination; each of the preceding with or without Cyclosporine A 0.5 uG/ml. Cells were harvested after three days, irradiated (3000R), then FACS analyzed or cocultured in graded numbers with freshly prepared naive (CD45RO negative) T lymphocytes. Allosensitization was assessed by pulsing at day 4 with $^3$H-TdR and harvesting 18 hours later.

Ionophore treatment resulted in a typical effect on HL-60, including marked upregulation of costimulatory molecules B7.1, B7.2, and ICAM-1. GM-CSF and IFN-gamma without ionophore upregulated MHC Class II but had no induction of costimulatory molecules. Thus, the combination of ionophore and cytokines enhanced MHC Class I expression compared to ionophore alone, and induced MHC Class II expression as well as costimulatory molecule expression.

Only two of the above groups were significantly allostimulatory to T cells, those cells which received ionophore treatment, and those cells which were treated with ionophore plus GM-CSF plus IFN-g, consistent with the induction of costimulatory molecule expression in both of these treatment groups. CsA treatment obliterated the allostimulatory capacity of the both ionophore treated groups, consistent with its blockade of costimulatory molecule expression. CsA treatment resulted in little or no blockade of ionophore/IFN-gamma's upregulation of HLA-DR, indicating it caused "mixed" modulations on HL-60 activation.

Thus, the antigen presenting activity of myeloid cells such as HL-60 cells and monocytes may be positively or negatively modulated to create a desired cellular phenotype having desired immunological characteristics.

Several frequent media ingredients—the antibiotic amphotericin B and endotoxin in the 0.1–1 ng/ml range (often present in antigens or serum in media) enhance calcium ionophore's effect. Other potential media ingredients—including glucocorticoid hormones, prostaglandins E1/E2, IL-10, TGF-beta.

When the presence of such enhancing and inhibiting agents is minimized, it is possible to see the effects which are solely due to calcium ionophore treatment. These effects can also be confirmed in serum-free media devoid of any proteins except albumin, transferrin and insulin. In addition, some inhibitory effects of the calcineurin inhibitor cyclosporine A (CsA) provide a very sensitive confirmation of calcium-dependence even under conditions where the sole effects on phenotype are due to culture conditions.

Other phenotypic changes which occur during calcium ionophore treatment, but which cannot be attributed in large part to calcium ionophore treatment per se include upregulation of HLA-DR expression, upregulation of HLA-ABC, upregulation of HLA-DQ, and upregulation of ICAM-1 (CD54). These effects were seen when amphotericin B and endotoxin were present in the culture medium of cells treated with calcium ionophore. Thus, markedly enhanced upregulation of HLA-DR, HLA-ABC, HLA-DQ, and ICAM-1 (CD54)occurs when agents such as amphotericin B, endotoxin, or adjunct cytokines are included during calcium ionophore treatment.

VII. Induction of an Activated Myeloid Dendritic Cell Phenotype in Bone Marrow Myeloid Progenitor Cells In addition to monocytes and HL-60 cells, bone marrow myeloid progenitor cells can also be induced to express the phenotype of activated myeloid dendritic cells. Current evidence indicates that circulating monocytes and immature DC are at least some of the time derived from a common bone marrow progenitor cell (Caux et al, *J. Exp. Med.* 184:695, 1996; Szabolcs et al, *Blood* 87:4520, 1996). The earliest stage of cell differentiation commonly isolable for bone marrow progenitors is the $CD34^{pos}$ cell. This cell type, sometimes termed a "stem cell," can be isolated from bone marrow, neonatal cord blood, or from peripheral adult blood.

Isolated $CD34^{pos}$ cells are typically cultured for the first five to seven days in stem cell factor (SCF, or c-KIT ligand) to promote rapid proliferation; concomitant addition of rhGM-CSF has been shown to favor expansion of myeloid progenitors; concomitant addition of rhTNF-alpha has been shown to favor or sustain DC differentiation.

Proliferation is largely complete by day 7 of culture, but differentiation continues for the next week. When cultured for a total of 12–14 days with these three cytokines, bone marrow-derived $CD34^{pos}$ cells develop into a mixed, predominantly myeloid population consisting of neutrophils (approximately 70%), monocytes (15%), inactive DC (10%), and activated DC (5%) (Szabolcs et al, *Blood* 87:4520, 1996).

As described above, circulating monocytes, DC, and myeloid leukemia cells each respond to calcium mobilization by rapidly acquiring the phenotype of an activated myeloid dendritic cell. Example 24 below demonstrates that bone marrow myeloid progenitor cells can also be induced to express the phenotype of activated myeloid dendritic cells.

EXAMPLE 24

Bone marrow-derived highly purified $CD34^{pos}$ cells were cultured for six days in medium containing 20% fetal calf serum, rhSCF, rhGM-CSF, and rhTNF-alpha. Proliferation during this period resulted in approximately six-fold expansion. Cells were centrifuged and replated in 24 well plates in fresh medium containing rhGM-CSF, and rhTNF-alpha but not rhSCF. In addition, individual wells were treated with varied doses of ionophore A23187. Wells were harvested 1, 2, and 6 days subsequently, subjected to FACS analysis or studied morphologically for DC characteristics utilizing polylysine-coated glass slides and Nomarski optics.

Wells which were not treated with ionophore retained a highly heterogeneous cellular composition both by FACS and morphologic analysis which persisted during the six days of observation; CD14 expression was heterogenous but common, and development of an activated dendritic cell phenotype was an infrequent event, confirming the reports of others (Szabolcs et al, *Blood* 87:4520, 1996). In contrast, wells treated with an optimal concentration of calcium ionophore (375–750 ng/ml) displayed a predominant dendritic cell immunophenotype by FACS within 20 hours of treatment, including marked CD14 downregulation, paralleling calcium ionophore's effect on periphal blood monocytes. This immunophenotype consisted of nearly uniform (>85% of cells), marked upregulation of B7.1, B7.2, ICAM-1, CD83, CD40 and CD1a; in addition, these cells expressed high levels of HLA-DR and HLA-ABC. Within 40 hours of treatment virtually all cells manifested dendritiform morphology.

Cells not treated with ionophore when replated at day 6 maintained good viability, and approximately twice as many cells were recovered 6 days later. Replated wells treated with an optimum converting dose of 375 ng/ml calcium ionophore also maintained good viability during the 6 day subsequent culture, with approximately 80% recovery). For absolute numbers of cells recovered, calcium ionophore treatment increased the yield of cells having the phenotype of an activated myeloid dendritic cell approximately threefold compared to wells without ionophore, and increased purity of cells with an activated myeloid dendritic cell phenotype at final harvest approximately six-fold.

Thus, pluripotent bone marrow myeloid progenitors have a capacity to rapidly commit and differentiate to an activated dendritic cell phenotype following calcium mobilization which closely parallels that of human peripheral blood monocytes.

VIII. Induction of an Activated Dendritic Cell Phenotype in Lymphoid Leukemia and Endothelial Cells Other cell types may also respond to calcium mobilization by upregulating molecules such as B7.1, B7.2, CD40, ICAM-1 and CD83 which may be critical for antigen presentation. The above data indicates that this appears to be a universal response of myeloid-origin cells such as monocytes, dendritic cells, and their bone marrow precursors.

Example 25 and 26 below demonstrate that lymphocytes and endothelial cells to respond at least partially to calcium ionophore treatment. In addition, myeloid leukemia lines can respond to calcium mobilization treatment analogously to normal myeloid cells, and it is likely that tumors of many different tissue types may also manifest similar features, at least in part.

EXAMPLE 25

Myeloid leukemia cell lines display marked upregulation of molecules linked to antigen-presentation and acquire increased T cell sensitizing capacity following calcium mobilization with either calcium ionophore or thapsigargin. Experiments conducted with two myeloid leukemia lines, the human myeloid leukemia line HL-60 and the mouse cell line WEHI-3, demonstrate that these cells display markedly increased costimulatory molecule expression following calcium mobilization.

The response of HL-60 cells to optimal doses of calcium ionophore or thapsigargin is many ways kinetically analogous to the response of peripheral blood monoytes. Within 20 hours of treatment uniform de novo expression of CD83, ICAM-1, B7.1, and B7.2 occurs. During the next several days, CD83 expression declines whereas costimulatory molecule expression is relatively sustained. In addition, increased expression of CD40 and CD1a, as well as increased acquisition of dendritiform morphologic characteristics, occurs between day 2 and day 4 of treatment.

HL-60 cells express HLA-ABC but lack HLA-DR, and the latter is not induced by calcium ionophore treatment alone. However, rhIFN-gamma treatment induces HLA-DR expression, which is markedly enhanced by calcium ionophore treatment; rhGM-CSF treatment has little effect alone, but enhances and/or sustains ionophore's upregulation of CD1a and B7.2. When treated with various combinations of ionophore, IFN-gamma and GM-CSF, then irradiated and cocultured with allogeneic T cells in 4 day proliferation assays, HL-60 cells treated with all three agents (ionophore, GM-CSF and IFN-gamma) displayed by far the most potent T cell sensitization capacity, consistent with their superior expression of costimulatory and MHC molecules.

Thus, calcium mobilization activates immuophenotypic and functional properties of efficient antigen-presenting cells in at least some malignancies of myeloid origin.

As described in Example 26 below, endothelial cells may also be induced to express CD40 and ICAM-1 in response to calcium ionophore treatment.

EXAMPLE 26

Endothelial cells were previously isolated from human umbilical vein (HUVEC), then cultured in IMEM with 20% fetal calf serum and rhEGF (endothelial growth factor). The cells in this experiment had undergone four previous passages to confluence and were trypsinized and reseeded in T25 flasks. After four days culture to reachieve confluence individual flasks were treated with several concentrations of calcium ionophore (180, 375 and 750 ng/ml). Two days later, cells were harvested by trypsinization and analyzed.

Cells treated with the higher concentrations of ionophore (375 and 750 ng/ml) upregulated ICAM-1 and CD40 expression, but failed to express detectable B7.1, B7.2, HLA-DR or CD83 either with or without ionophore treatment. HLA-ABC expression was present but unchanged by calcium ionophore treatment.

The lack of upregulation of many such markers may have been caused by loss of functional potential during repeated passage in culture. In view of the fact that constituitive expression of B7.2 on HUVEC as well as inducible expression of HLA-DR with IFN-gamma treatment has been reported in the literature,(Seino et al, Int Immunol 7:1331, 1995), it is likely that both B7.2 and HLA-DR may be upregulated with calcium mobilization treatment on earlier passaged endothelial cells, possibly in conjunction with cytokine treatments.

Human lymphocytes upregulate molecules associated with improve antigen-presenting capacity following calcium ionophore treatment. As described above, monocytes present as a 15% subpopulation of unfractionated PBMC achieved differentiation to an activated dendritic cell phenotype during calcium ionophore treatment even without further purification. In these same experiments we examined the effects of calcium ionophore on other subpopulations within the PBMC. The results are described in Example 27 below.

EXAMPLE 27

PBMC were prepared by leukapheresis and Ficoll-Hypaque and placed in culture. Since the cells were never elutriated and no adherence step was performed, these cultures included large numbers of T, B, and NK lymphocytes as well as monocytes. The medium was our standard RPMI 10% human AB serum with antibiotics including amphotericin B. Cells were either untreated or treated for 40 hours with calcium ionophore A23187 750 mg/ml. Cells were then harvested and analyzed by FACS. Cells were stained with FITC conjugated anti-CD3, anti-CD40, anti-CD57, anti-CD14, or the combination; in addition cells were stained with PE conjugated control antibodies, anti-B7.1, anti-B7.2, etc. In this way the effect of calcium ionophore treatment on each parameter could be clearly delineated.

The T lymphocyte subpopulation within the PBMC was 62–72% of the recovered cells; calcium ionophore treatment had marked effects on the T cell subpopulation, including B7.2 upregulation (10 fold increase over culture without ionophore), ICAM-1 upregulation (3.3 fold) HLA-DR (6 fold), and CD40 (4 fold). The B cell subpopulation was 8–11% of the total, and although overall upregulation of surface markers was of a lower magnitude than for T cells, a subpopulation of B cells developed marked B71 and B72 expression during calcium ionophore treatment. The NK subpopulation (22–23% of total PBMC) displayed negligible upregulation of surface markers in response to calcium ionophore.

Thus, a large subpopulation of T lymphocytes and smaller subpopulation of B lymphocytes respond to calcium ionophore treatment by upregulation of surface costimulatory, MHC, and/or other molecules which may result in improved antigen presentation. Such upregulation may provide usefully enhanced antigen-presenting activity when PBMC are calcium-ionophore treated to create a source of activated dendritic cells. In addition, these data suggest that tumors of lymphoid origin, including leukemias and lymphomas, may upregulate such molecules analogously to the myeloid leukemia HL60's upregulation of ADC-associated markers.

As described in Example 28 below, autologous dendritic cells or monocytes which have been induced to develop the phenotype of activated myeloid dendritic cells may be used to treat cancer. In fact, the use of activated dendritic cells as a cancer treatment has met with some success. Hsu, F. J. et al., Natl. Med. 1996 2:52–58.

EXAMPLE 28

Dendritic cell or monocyte enriched fractions, or combinations of dendritic cells and monocytes, are isolated from a patient in need of treatment for prostate cancer by leukapheresis, citrate buffer rinse and CCE as described above. Multiple elutriation fractions are collected to maximize the separation of lymphocytes, monocytes and dendritic cell, and neutrophil contaminated fractions. After pooling all post 140 fractions which are not significantly contaminated with neutrophils, the cells in the pooled fractions are contacted with an agent which increases the intracellular calcium concentration, such as 750 mg/ml A23187 in 10% serum from a donor having an AB blood type. For example, the 120, 140, 150, 170, 190, 200 and rotor off fractions may be pooled and induced. The pooled fractions are then incubated for 40 hours with a prostate tumor cell lysate from prostate cancer cells previously obtained from a biopsy of the patient. This incubation activates the dendritic cells and monocytes which have been induced to express the phenotype of activated myeloid dendritic cells to present prostate tumor cell antigens.

Alternatively, peripheral blood mononuclear cell preparations obtained as described above may be induced with agents which increase the intracellular calcium level, such as calcium ionophores, to enhance their antigen presenting activity. The cells are then incubated with the prostate tumor antigens, causing them to present the tumor antigen.

In yet another embodiment bone marrow myeloid progenitor cells are incubated with agents which increase the intracellular calcium level, such as calcium ionophores, to enhance their antigen presenting activity. The cells are then incubated with the prostate tumor antigens, causing them to present the tumor antigen.

After incubation in the presence of the prostate tumor antigens, the cells are reintroduced into the patient. The cells may be introduced into the patient intravenously or via any route which enables the cells to present antigen to immune cells, which generate then generate an immune response. Three weeks later, a reduction in the size of the prostate tumor is noticed due to activation of the patient's immune system via the introduced, activated dendritic cells.

Although this is one example of a possible antigen that could be used in the present technique, one of ordinary skill in the art will recognize that other similar antigens could also function effectively. For example, dendritic cells can be challenged with antigens from the surface of HIV-1, or other disease-carrying agent and then reintroduced into a patient that has AIDS. Other types of disease-carrying agents, such as cancer cells of the breast, brain, liver or stomach are also anticipated to function effectively to activate dendritic cells to present tumor antigens in the methods of the present invention. In this manner, the physician can stimulate an anti-cancer antigen response in vitro, and then reintroduce the patients own antigen-presenting dendritic cells as a method of increasing the immune response to the tumor cells.

As described above, myeloid and lymphoid cells upregulate cell surface markers involved in antigen presentation when the level of intracellular calcium is elevated. This phenomenon may be exploited to treat both myeloid and lymphoid leukemias as described in Example 29 below.

EXAMPLE 29

Lyphoid or myeloid leukemia cells are obtained from the peripheral blood of a subject using the techniques described above. Thereafter, the cells are contacted with an agent, such as a calcium ionophore, which increases the intracellular calcium level, thereby inducing the expression of cell surface markers which increase the antigen presenting ability of the cells. The induced cells are then treated with gamma irradiation or agents which prevent them from proliferating and transferred back into the subject from which they were taken. The induced cells present leukemia specific antigens to the immune system of the subject, generating an immune response which kills the leukemic cells and produces an improvement in the clinical condition of the subject.

Preferred features of the present invention have been described above. However, the true scope of the invention is not limited to only those embodiments illustrated in the Detailed Description, but should only be limited by the scope of the following claims. All references and patent applications referred to herein are incorporated herein by reference in their entirety.

TABLE 3

Summary Of Steps for Isolating Dendritic Cells.

1. Patient or donor leukapheresis (LP) using platelet-rich, neutrophil-poor collection mode (e.g., on CS3000 using neutrophil-poor software program)
2. LP collected cells centrifuged, washed in citrate buffer to remove interfering proteins, room temperature. Resuspend cells in HBSS without $Ca^{++}/Mg^{++}$ or EDTA
3. Washed cell aliquot loaded (conservative cell load) at room temperature onto elutriator (CCE). Following fractions collected: 120, 140, 150, 180, 190, 200, Rotor off (R/O) (or all fractions after 140 if these fractions are significantly free of neutrophils)
4. Fractions collected immediately on ice to prevent cell adherence
5. Coulter counter histogram used for rapid analysis of neutrophil contamination in later fractions; discard R/O, etc., if contamination >10%
6. Pool and/or cryopreserve appropriate fractions (120 + 140 pooled as a lymphocyte fraction unless 120 contaminated from overload, in which case 140 alone used as lymphocyte fraction; 150 + 160 + 170 + 180 + 190 usually pooled as APC (monocyte + DC) fraction; however, 160 and 170 fractions can be used alone as "highly DC" enriched fractions.
7. Triple color FACS analysis for quality control of 1–6 step collection.
8. APC fraction placed in short term culture (either fresh cells or thawed cryopreserved cells) to upregulate necessary APC molecules including B7.1 and HLA-DQ. Calcium ionophore typically used to activate DC subpopulation and convert bulk monocyte population over to activated DC phenotype. Specific recombinant cytokine combinations added to culture in some instances (e.g., rhIL-12, rhGM-CSF, rhIL-4 and rhIL-2, gamma-interferon, TNF-alpha) as well as agents such as endotoxin or amphotericin B
9. Cultured/activated, antigen pulsed APCs harvested using $Ca^{++}/Mg^{++}$ free medium (HBSS or PBS) with collection into ice cold buffer in tubes kept on ice.
10. Triple color FACS analysis for quality control of APC activation
11. Use activated, antigen pulsed APCs to stimulate growth of T lymphocytes in culture or reinject into patient as a "vaccine."

What is claimed is:

1. A method of increasing the antigen presenting ability of leukemia cells comprising contacting said leukemia cells with an agent which elevates the intracellular calcium concentration to a level sufficient to increase said antigen presenting ability.

2. The method of claim 1, wherein said agent comprises a calcium ionophore.

3. The method of claim 2, wherein said calcium ionophore is selected from the group consisting of A23187 and ionomycin.

4. The method of claim 1, wherein said leukemia cells increase their level of expression of B7.1.

5. The method of claim 1, wherein said leukemia cells increase their level of expression of B7.2.

6. The method of claim 1, wherein said leukemia cells increase their level of expression of ICAM-1.

7. The method of claim 1, wherein said leukemia cells increase their level of expression of CD83.

8. The method of claim 1, wherein said leukemia cells increase their level of expression of B7.1, B7.2, and ICAM-1.

9. The method of claim 8, wherein said leukemia cells increase their level of expression of CD83.

10. The method of claim 1, wherein said leukemia cells are myeloid leukemia cells.

11. The method of claim 1, wherein said leukemia cells are lymphoid leukemia cells.

12. The method of claim 1, further comprising contacting T cells with leukemia cells which have been treated with said agent.

13. A method of increasing the antigen presenting ability of leukemia cells comprising:

obtaining a population of cells from a subject comprising leukemia cells in order to increase the antigen presenting ability of said leukemia cells; and contacting said leukemia cells with an agent which elevates the intracellular calcium concentration to a level sufficient to increase the antigen presenting ability of said leukemia cells.

14. The method of claim 13, wherein said agent comprises a calcium ionophore.

15. The method of claim 13, wherein said leukemia cells increase their level of expression of B7.1.

16. The method of claim 13, wherein said leukemia cells increase their level of expression of B7.2.

17. The method of claim 13, wherein said leukemia cells increase their level of expression of ICAM-1.

18. The method of claim 13, wherein said leukemia cells increase their level of expression of CD83.

19. The method of claim 13, wherein said leukemia cells increase their level of expression of B7.1, B7.2, and ICAM-1.

20. The method of claim 13, wherein said agent elevates the intracellular calcium level by blocking the export of calcium out of the cytoplasm.

21. The method of claim 13, wherein said agent comprises adenovirus.

22. The method of claim 14, wherein said calcium ionophore is selected from the group consisting of A23187 and ionomycin.

23. The method of claim 13, wherein said agent activates the calcineurin pathway.

24. The method of claim 13, further comprising contacting said leukemia cells which have been contacted with said agent with a compound selected from the group consisting of rhGM-CSF and IFN-gamma.

25. The method of claim 13, further comprising contacting said leukemia cells which have been contacted with said agent with a compound selected from the group consisting of glucocorticoids, prostaglandins, and TGF-beta.

26. The method of claim 13, further comprising contacting said leukemia cells which have been contacted with said agent with endotoxin.

27. The method of claim 13, further comprising the step of contacting T cells with said leukemia cells which have been contacted with said agent.

28. The method of claim 13, further comprising measuring the antigen presenting ability of said leukemia cells which have been contacted with said agent.

29. The method of claim 13, further comprising the step of transferring said leukemia cells which have been contacted with said agent to a subject.

30. The method of claim 29, wherein said obtaining step comprises obtaining said leukemia cells from said subject.

31. The method of claim 29, further comprising treating said leukemia cells with an agent which prevents them from replicating.

* * * * *